(12) United States Patent
Hanson et al.

(10) Patent No.: US 7,229,464 B2
(45) Date of Patent: Jun. 12, 2007

(54) FILTER DELIVERY AND RETRIEVAL DEVICE

(75) Inventors: Scott M. Hanson, Savage, MN (US); Andrew J. Dusbabek, Dayton, MN (US); Gary L. Hendrickson, Big Lake, MN (US)

(73) Assignee: Scimed Life Systems, Inc., Maple Grove, MN (US)

( * ) Notice: Subject to any disclaimer, the term of this patent is extended or adjusted under 35 U.S.C. 154(b) by 391 days.

(21) Appl. No.: 10/621,599

(22) Filed: Jul. 17, 2003

(65) Prior Publication Data

US 2004/0019363 A1   Jan. 29, 2004

Related U.S. Application Data

(63) Continuation of application No. 09/801,263, filed on Mar. 7, 2001, now Pat. No. 6,616,681.

(60) Provisional application No. 60/238,188, filed on Oct. 5, 2000.

(51) Int. Cl.
*A61M 29/00* (2006.01)
(52) U.S. Cl. ................................. 606/200
(58) Field of Classification Search ............... 606/113, 606/114, 127, 200; 623/1.11, 1.12, 1.2; 600/585, 600/434
See application file for complete search history.

(56) References Cited

U.S. PATENT DOCUMENTS

| | | | |
|---|---|---|---|
| 3,472,230 A | 10/1969 | Fogarty | 128/328 |
| 3,592,186 A | 7/1971 | Oster | 128/2 |
| 3,683,904 A | 8/1972 | Forster | 128/127 |
| 3,889,657 A | 6/1975 | Baumgarten | 128/2 |
| 3,952,747 A | 4/1976 | Kimmell, Jr. | 128/303 |
| 3,996,938 A | 12/1976 | Clark, III | 128/348 |
| 4,046,150 A | 9/1977 | Schwartz et al. | 128/328 |
| 4,425,908 A | 1/1984 | Simon | 128/1 |
| 4,447,227 A | 5/1984 | Kotsanis | 604/95 |
| 4,580,568 A | 4/1986 | Gianturco | 128/345 |
| 4,590,938 A | 5/1986 | Segura et al. | 128/328 |
| 4,619,246 A | 10/1986 | Molgaard-Nielsen et al. | 128/1 |
| 4,631,052 A | 12/1986 | Kensey | 604/22 |
| 4,643,184 A | 2/1987 | Mobin-Uddin | 128/303 |
| 4,650,466 A | 3/1987 | Luther | 604/95 |
| 4,662,885 A | 5/1987 | DiPisa, Jr. | 623/12 |

(Continued)

*Primary Examiner*—Kevin T. Truong
(74) *Attorney, Agent, or Firm*—Crompton, Seager & Tufte LLC

(57) ABSTRACT

Methods and devices for providing temporary placement of a filter in a blood vessel are disclosed. A filter delivery system in accordance with one exemplary embodiment of the present invention includes a catheter having an elongate shaft and a tubular member disposed within a shaft lumen defined by the elongate shaft. The elongate shaft also includes a proximal end, a distal end, and a wall defining the shaft lumen. The tubular member has a first end fixed to the wall of the elongate shaft, and a second end disposed within the shaft lumen. The tubular member defines a guidewire lumen that is in fluid communication with a distal guidewire port defined by the second end of the tubular member. The catheter also includes a proximal guidewire port extending through the wall of the elongate shaft. A filter may be disposed within a distal portion of the shaft lumen. A distal end of a guidewire is fixed to the filter. The guidewire preferably extends through the distal guidewire port, the guidewire lumen, and the proximal guidewire port.

18 Claims, 24 Drawing Sheets

U.S. PATENT DOCUMENTS

| | | | |
|---|---|---|---|
| 4,705,517 A | 11/1987 | DiPisa, Jr. | 623/12 |
| 4,706,671 A | 11/1987 | Weinrib | 128/348 |
| 4,723,549 A | 2/1988 | Wholey et al. | 128/344 |
| 4,728,319 A | 3/1988 | Masch | 604/22 |
| 4,733,665 A | 3/1988 | Palmaz | 128/343 |
| 4,762,129 A | 8/1988 | Bonzel | 606/194 |
| 4,790,812 A | 12/1988 | Hawkins, Jr. et al. | 604/22 |
| 4,790,813 A | 12/1988 | Kensey | 604/22 |
| 4,794,928 A | 1/1989 | Kletschka | 128/344 |
| 4,794,931 A | 1/1989 | Yock | 128/660 |
| 4,800,882 A | 1/1989 | Gianturco | 128/343 |
| 4,807,626 A | 2/1989 | McGirr | 128/328 |
| 4,842,579 A | 6/1989 | Shiber | 606/22 |
| 4,857,045 A | 8/1989 | Rydell | 604/22 |
| 4,857,046 A | 8/1989 | Stevens et al. | 604/22 |
| 4,867,157 A | 9/1989 | McGurk-Burleson et al. | 128/305 |
| 4,873,978 A | 10/1989 | Ginsburg | 128/345 |
| 4,898,575 A | 2/1990 | Fischell et al. | 604/22 |
| 4,907,336 A | 3/1990 | Gianturco | 29/515 |
| 4,921,478 A | 5/1990 | Solano et al. | 604/53 |
| 4,921,484 A | 5/1990 | Hillstead | 604/104 |
| 4,926,858 A | 5/1990 | Gifford, III et al. | 606/159 |
| 4,950,277 A | 8/1990 | Farr | 606/159 |
| 4,955,895 A | 9/1990 | Sugiyama et al. | 606/194 |
| 4,957,482 A | 9/1990 | Shiber | 604/22 |
| 4,969,891 A | 11/1990 | Gewertz | 606/200 |
| 4,979,951 A | 12/1990 | Simpson | 606/159 |
| 4,986,807 A | 1/1991 | Farr | 604/22 |
| 4,998,539 A | 3/1991 | Delsanti | 128/898 |
| 5,002,560 A | 3/1991 | Machold et al. | 606/198 |
| RE33,569 E | 4/1991 | Gifford, III et al. | 606/159 |
| 5,007,896 A | 4/1991 | Shiber | 604/22 |
| 5,007,917 A | 4/1991 | Evans | 606/170 |
| 5,011,488 A | 4/1991 | Ginsburg | 606/159 |
| 5,019,088 A | 5/1991 | Farr | 606/159 |
| 5,040,548 A | 8/1991 | Yock | 128/898 |
| 5,041,126 A | 8/1991 | Gianturco | 606/195 |
| 5,053,008 A | 10/1991 | Bajaj | 604/104 |
| 5,053,044 A | 10/1991 | Mueller et al. | 606/159 |
| 5,071,407 A | 12/1991 | Termin et al. | 604/104 |
| 5,071,425 A | 12/1991 | Gifford, III et al. | 606/159 |
| 5,085,662 A | 2/1992 | Willard | 606/159 |
| 5,087,265 A | 2/1992 | Summers | 606/159 |
| 5,100,423 A | 3/1992 | Fearnot | 606/15 |
| 5,100,424 A | 3/1992 | Jang et al. | 606/159 |
| 5,100,425 A | 3/1992 | Fischell et al. | 606/159 |
| 5,102,415 A | 4/1992 | Guenther et al. | 606/159 |
| 5,104,399 A | 4/1992 | Lazarus | 623/1 |
| 5,108,419 A | 4/1992 | Reger et al. | 606/200 |
| 5,133,733 A | 7/1992 | Rasmussen et al. | 606/200 |
| 5,135,531 A | 8/1992 | Shiber | 606/159 |
| 5,152,771 A | 10/1992 | Sabbaghian et al. | 606/159 |
| 5,152,777 A | 10/1992 | Goldberg et al. | 606/200 |
| 5,160,342 A | 11/1992 | Reger et al. | 606/200 |
| 5,171,233 A | 12/1992 | Amplatz et al. | 604/281 |
| 5,190,546 A | 3/1993 | Jervis | 606/78 |
| 5,195,955 A | 3/1993 | Don Michael | 604/22 |
| 5,224,953 A | 7/1993 | Morgentaler | 606/192 |
| 5,306,286 A | 4/1994 | Stack et al. | 606/198 |
| 5,314,444 A | 5/1994 | Gianturco | 606/195 |
| 5,314,472 A | 5/1994 | Fontaine | 623/12 |
| 5,318,576 A | 6/1994 | Plassche, Jr. et al. | 606/159 |
| 5,329,942 A | 7/1994 | Gunther et al. | 128/898 |
| 5,330,484 A | 7/1994 | Gunther | 606/128 |
| 5,330,500 A | 7/1994 | Song | 606/198 |
| 5,350,398 A | 9/1994 | Pavcnik et al. | 606/200 |
| 5,354,310 A | 10/1994 | Garnic et al. | 606/198 |
| 5,356,423 A | 10/1994 | Tihon et al. | 606/194 |
| 5,360,401 A | 11/1994 | Turnland et al. | 604/96 |
| 5,366,464 A | 11/1994 | Belknap | 606/159 |
| 5,366,473 A | 11/1994 | Winston et al. | 606/198 |
| 5,368,557 A | 11/1994 | Nita et al. | |
| 5,370,616 A | 12/1994 | Keith et al. | 604/102 |
| 5,370,657 A | 12/1994 | Irie | 606/200 |
| 5,370,683 A | 12/1994 | Fontaine | 623/1 |
| 5,376,100 A | 12/1994 | Lefebvre | 606/180 |
| 5,383,887 A | 1/1995 | Nadal | 606/200 |
| 5,383,892 A | 1/1995 | Cardon et al. | 606/198 |
| 5,383,926 A | 1/1995 | Lock et al. | 623/1 |
| 5,387,235 A | 2/1995 | Chuter | 623/1 |
| 5,395,349 A | 3/1995 | Quiachon et al. | 604/248 |
| 5,397,345 A | 3/1995 | Lazarus | 623/1 |
| 5,405,377 A | 4/1995 | Cragg | 623/1 |
| 5,409,454 A | 4/1995 | Fischell et al. | 604/22 |
| 5,415,630 A | 5/1995 | Gory et al. | 604/53 |
| 5,419,774 A | 5/1995 | Willard et al. | 604/22 |
| 5,421,832 A | 6/1995 | Lefebvre | 604/53 |
| 5,423,742 A | 6/1995 | Theron | 604/28 |
| 5,423,885 A | 6/1995 | Williams | 623/1 |
| 5,425,765 A | 6/1995 | Tiefenbrun et al. | 623/12 |
| 5,443,498 A | 8/1995 | Fontaine | 623/1 |
| 5,449,372 A | 9/1995 | Schmaltz et al. | 606/198 |
| 5,456,667 A | 10/1995 | Ham et al. | 604/107 |
| 5,462,529 A | 10/1995 | Simpson et al. | 604/101 |
| 5,466,222 A | 11/1995 | Ressemann et al. | 604/96 |
| 5,476,104 A | 12/1995 | Sheahon | 128/757 |
| 5,484,418 A | 1/1996 | Quiachon et al. | 604/167 |
| 5,507,767 A | 4/1996 | Maeda et al. | 606/198 |
| 5,512,044 A | 4/1996 | Duer | 604/22 |
| 5,527,354 A | 6/1996 | Fontaine et al. | 623/1 |
| 5,534,007 A | 7/1996 | Germain et al. | 606/108 |
| 5,536,242 A | 7/1996 | Willard et al. | 604/30 |
| 5,540,707 A | 7/1996 | Ressemann et al. | 606/159 |
| 5,549,626 A | 8/1996 | Miller et al. | 606/200 |
| 5,562,724 A | 10/1996 | Vorwerk et al. | 623/1 |
| 5,569,274 A | 10/1996 | Rapacki et al. | 606/158 |
| 5,569,275 A | 10/1996 | Kotula et al. | 606/159 |
| 5,634,897 A | 6/1997 | Dance et al. | 604/35 |
| 5,658,296 A | 8/1997 | Bates et al. | 606/127 |
| 5,662,671 A | 9/1997 | Barbut et al. | 606/170 |
| 5,669,933 A | 9/1997 | Simon et al. | 600/200 |
| 5,681,347 A | 10/1997 | Cathcart et al. | 606/200 |
| 5,695,519 A | 12/1997 | Summers et al. | 606/200 |
| 5,709,704 A | 1/1998 | Nott et al. | 606/200 |
| 5,720,764 A | 2/1998 | Naderlinger | 606/200 |
| 5,728,066 A | 3/1998 | Daneshvar | 604/96 |
| 5,728,067 A | 3/1998 | Enger | 604/102 |
| 5,746,758 A | 5/1998 | Nordgren et al. | 606/159 |
| 5,749,848 A | 5/1998 | Jang et al. | 604/53 |
| 5,769,816 A | 6/1998 | Barbut et al. | 604/96 |
| 5,779,671 A | 7/1998 | Ressemann et al. | |
| 5,779,716 A | 7/1998 | Cano et al. | 606/114 |
| 5,792,157 A | 8/1998 | Mische et al. | |
| 5,792,300 A | 8/1998 | Inderbitzen et al. | 156/244 |
| 5,795,322 A | 8/1998 | Boudewijn | 604/22 |
| 5,797,952 A | 8/1998 | Klein | 606/198 |
| 5,800,457 A | 9/1998 | Gelbfish | 606/200 |
| 5,800,525 A | 9/1998 | Bachinski et al. | 623/1 |
| 5,810,874 A | 9/1998 | Lefebvre | 606/200 |
| 5,814,064 A | 9/1998 | Daniel et al. | 606/200 |
| 5,817,102 A | 10/1998 | Johnson et al. | 606/108 |
| 5,827,324 A | 10/1998 | Cassell et al. | 606/200 |
| 5,833,644 A | 11/1998 | Zadno-Azizi et al. | 604/52 |
| 5,833,650 A | 11/1998 | Imran | 604/53 |
| 5,846,260 A | 12/1998 | Maahs | 606/200 |
| 5,848,964 A | 12/1998 | Samuels | 600/200 |
| 5,876,367 A | 3/1999 | Kaganov et al. | 604/8 |
| 5,893,867 A | 4/1999 | Bagaoisan et al. | 606/198 |
| 5,893,869 A | 4/1999 | Barnhart | 606/200 |
| 5,895,399 A | 4/1999 | Barbut et al. | 606/159 |
| 5,902,263 A | 5/1999 | Patterson et al. | 604/22 |
| 5,906,618 A | 5/1999 | Larson, III | 606/108 |
| 5,908,435 A | 6/1999 | Samuels | 606/200 |

| Patent No. | Date | Inventor | Class |
|---|---|---|---|
| 5,910,154 A | 6/1999 | Tsugita et al. | 606/200 |
| 5,911,734 A | 6/1999 | Tsugita et al. | 606/200 |
| 5,916,192 A | 6/1999 | Nita et al. | |
| 5,916,193 A | 6/1999 | Stevens et al. | 604/53 |
| 5,925,016 A | 7/1999 | Chornenky et al. | 604/96 |
| 5,925,060 A | 7/1999 | Forber | 606/191 |
| 5,925,062 A | 7/1999 | Purdy | 606/200 |
| 5,925,063 A | 7/1999 | Khosravi | 606/200 |
| 5,928,203 A | 7/1999 | Davey et al. | 604/247 |
| 5,928,218 A | 7/1999 | Gelbfish | 604/540 |
| 5,934,284 A | 8/1999 | Plaia et al. | 128/898 |
| 5,935,139 A | 8/1999 | Bates | 606/159 |
| 5,938,645 A | 8/1999 | Gordon | 604/264 |
| 5,941,869 A | 8/1999 | Patterson et al. | 604/508 |
| 5,941,896 A | 8/1999 | Kerr | 606/200 |
| 5,947,995 A | 9/1999 | Samuels | 606/200 |
| 5,951,585 A | 9/1999 | Cathcart et al. | 606/198 |
| 5,954,745 A | 9/1999 | Gertler et al. | 606/200 |
| 5,976,172 A | 11/1999 | Homsma et al. | 606/200 |
| 5,980,555 A | 11/1999 | Barbut et al. | |
| 5,989,210 A | 11/1999 | Morris et al. | 604/22 |
| 5,989,271 A | 11/1999 | Bonnette et al. | 606/159 |
| 5,989,281 A | 11/1999 | Barbut et al. | 606/200 |
| 5,993,469 A | 11/1999 | McKenzie et al. | 606/159 |
| 5,997,557 A | 12/1999 | Barbut et al. | 606/159 |
| 6,001,118 A | 12/1999 | Daniel et al. | 606/200 |
| 6,007,557 A | 12/1999 | Ambrisco et al. | 606/200 |
| 6,010,522 A | 1/2000 | Barbut et al. | 606/200 |
| 6,013,085 A | 1/2000 | Howard | 606/108 |
| 6,027,520 A | 2/2000 | Tsugita et al. | 606/200 |
| 6,042,598 A | 3/2000 | Tsugita et al. | |
| 6,051,014 A | 4/2000 | Jang | 606/200 |
| 6,051,015 A | 4/2000 | Maahs | 606/200 |
| 6,053,932 A | 4/2000 | Daniel et al. | 606/200 |
| 6,059,814 A | 5/2000 | Ladd | 606/200 |
| 6,066,149 A | 5/2000 | Samson et al. | |
| 6,066,158 A | 5/2000 | Engelson et al. | |
| 6,068,645 A | 5/2000 | Tu | 606/200 |
| 6,074,357 A | 6/2000 | Kaganov et al. | 604/8 |
| 6,086,605 A | 7/2000 | Barbut et al. | 606/200 |
| 6,117,154 A | 9/2000 | Barbut et al. | |
| 6,123,720 A * | 9/2000 | Anderson et al. | 623/1.12 |
| 6,129,739 A | 10/2000 | Khosravi | 606/200 |
| 6,136,016 A | 10/2000 | Barbut et al. | |
| 6,142,987 A | 11/2000 | Tsugita | 604/500 |
| 6,152,946 A | 11/2000 | Broome et al. | 606/200 |
| 6,165,179 A | 12/2000 | Cathcart et al. | 606/108 |
| 6,165,200 A | 12/2000 | Tsugita et al. | 606/200 |
| 6,168,579 B1 | 1/2001 | Tsugita | 604/96 |
| 6,171,327 B1 | 1/2001 | Daniel et al. | 606/200 |
| 6,171,328 B1 | 1/2001 | Addis | |
| 6,179,851 B1 | 1/2001 | Barbut et al. | 606/159 |
| 6,179,859 B1 | 1/2001 | Bates et al. | 606/200 |
| 6,179,861 B1 | 1/2001 | Khosravi et al. | 606/200 |
| 6,193,793 B1 | 2/2001 | Long et al. | 106/284 |
| 6,203,561 B1 | 3/2001 | Ramee et al. | 606/200 |
| 6,206,868 B1 | 3/2001 | Parodi | |
| 6,214,026 B1 | 4/2001 | Lepak et al. | 606/200 |
| 6,221,006 B1 | 4/2001 | Dubrul et al. | |
| 6,224,620 B1 | 5/2001 | Maahs | |
| 6,231,544 B1 | 5/2001 | Tsugita et al. | |
| 6,235,044 B1 | 5/2001 | Root et al. | |
| 6,235,045 B1 | 5/2001 | Barbut et al. | |
| 6,238,412 B1 | 5/2001 | Dubrul et al. | |
| 6,245,087 B1 | 6/2001 | Addis | |
| 6,245,088 B1 | 6/2001 | Lowery | |
| 6,245,089 B1 | 6/2001 | Daniel et al. | |
| 6,258,115 B1 | 7/2001 | Dubrul | |
| 6,264,663 B1 | 7/2001 | Cano | |
| 6,264,672 B1 | 7/2001 | Fisher | |
| 6,270,513 B1 | 8/2001 | Tsugita et al. | |
| 6,277,138 B1 | 8/2001 | Levinson et al. | |
| 6,277,139 B1 | 8/2001 | Levinson et al. | |
| 6,280,413 B1 | 8/2001 | Clark et al. | |
| 6,287,321 B1 | 9/2001 | Jang | |
| 6,290,710 B1 | 9/2001 | Cryer et al. | |
| 6,309,399 B1 | 10/2001 | Barbut et al. | |
| 6,319,268 B1 | 11/2001 | Ambrisco et al. | |
| 6,344,049 B1 | 2/2002 | Levinson et al. | |
| 6,616,679 B1 * | 9/2003 | Khosravi et al. | 606/200 |

* cited by examiner

FILTER DELIVERY AND RETRIEVAL DEVICE

CROSS REFERENCE TO RELATED APPLICATION

This is a continuation of application Ser. No. 09/801,263 filed on Mar. 7, 2001 now U.S. Pat. No. 6,616,681 which in turn claims the benefit of U.S. Provisional Application Ser. No. 60/238,188 filed on Oct. 5, 2000.

FIELD OF THE INVENTION

The present invention relates generally to devices and methods for treating occluded or stenoic blood vessels. More particularly, the present invention relates to devices and methods for providing temporary placement of a filter in a blood vessel during a procedure to remove an occlusion or stenosis.

BACKGROUND OF THE INVENTION

It is critical that the heart muscle be well oxygenated so that the blood pumping action of the heart is not impaired. Blood vessels which have become occluded (blocked) or stenotic (narrowed) may interrupt the oxygen supply to the heart muscle.

Occluded or stenotic blood vessels may be treated with a number of medical procedures including angioplasty and atherectomy. Angioplasty techniques such as percutaneous transluminal angioplasty (PTA) and percutaneous transluminal coronary angioplasty (PTCA) are relatively non-invasive methods of treating a stenotic lesion. These angioplasty techniques typically involve the use of a guidewire and a balloon catheter. In these procedures, a balloon catheter is advanced over a guidewire such that the balloon is positioned proximate a restriction in a diseased vessel. The balloon is then inflated and the restriction in the vessel is opened. During an atherectomy procedure, the stenotic lesion is mechanically cut or abraded away from the blood vessel wall using an atherectomy catheter.

During atherectomy procedures, stenotic debris that is separated from the stenosis may be free to flow within the lumen of the vessel. If this debris enters the circulatory system, it may facilitate the formation of an occlusion in the neural vasculature, or in the lungs, both of which are highly undesirable. An occlusion in the neural vasculature may cause a stroke, and an occlusion in the lungs may interfere with the oxygenation of the blood. During angioplasty procedures, stenotic debris may also break loose due to manipulation of the blood vessel.

SUMMARY OF THE INVENTION

The present invention relates generally to devices and methods for treating occluded or stenoic blood vessels. More particularly, the present invention relates to devices and methods for providing temporary placement of a filter in a blood vessel during a procedure to remove an occlusion or stenosis. A filter delivery system in accordance with one exemplary embodiment of the present invention includes a catheter having an elongate shaft and a tubular member disposed within a shaft lumen defined by the elongate shaft. The elongate shaft also includes a proximal end, a distal end, and a wall defining the shaft lumen. The tubular member has a first end fixed to the wall of the elongate shaft, and a second end disposed within the shaft lumen. The tubular member defines a guidewire lumen that is in fluid communication with a distal guidewire port defined by the second end of the tubular member. The catheter also includes a proximal guidewire port extending through the wall of the elongate shaft.

A filter may be disposed within a distal portion of the shaft lumen. A distal end of a guidewire is preferably fixed to the filter. The guidewire preferably extends through the distal guidewire port, the guidewire lumen, and the proximal guidewire port. The elongate shaft of the catheter may be moved proximally relative to the guidewire so that the filter is disposed outside of the shaft lumen. The filter is preferably free to assume an expanded configuration when it is outside of the shaft lumen.

The catheter may be moved relative to the guidewire, for example, by grasping a proximal portion of the guidewire and applying a pulling force to a hub of the catheter. The pulling force may be applied to the hub until the filter is deployed in the expanded configuration. The pulling force may also be continued until the catheter is removed from the blood vessel. Once the catheter has been removed from the blood vessel, the guidewire may be utilized to guide additional catheters (e.g., balloon catheters, atherectomy catheters, etc.) as they are advanced through the blood vessel.

A wire gripper may be used to aid in grasping the guidewire. One exemplary embodiment of a wire gripper includes a handle and a plurality of jaws for grasping the guidewire. A knurl nut fitting is used to urge the jaws against the guidewire.

An additional exemplary embodiment of a filter delivery system in accordance with the present invention includes a catheter having an elongate shaft and a hub disposed about the elongate shaft proximate the proximal end thereof. A slider is disposed in sliding engagement with a cavity of the hub. The slider includes a wire lock having a plurality of jaws. The wire lock may be used to selectively fix a proximal portion of a guidewire to the slider. A distal end of the guidewire is preferably fixed to a filter which is disposed in a shaft lumen of the catheter.

During a procedure to deliver the filter to a target location in a blood vessel, the hub and the shaft of the catheter may be moved proximally relative to the slider and the guidewire. When the hub is moved proximally relative to slider, the filter is urged out of the shaft lumen of the catheter. Once the filter is out of the shaft lumen it is free to assume an expanded configuration. The sliding relationship between the slider and the hub gives the user of the filter deployment system a defined distance to move the slider relative to the hub when deploying the filter.

Yet another exemplary embodiment of a filter delivery system in accordance with the present invention includes a catheter having an elongate shaft including a proximal portion, a distal portion, and a longitudinally collapsible portion disposed between the proximal portion and the distal portion. A ring is fixed to the distal portion of the elongate shaft distally of the collapsible portion. A pull wire is disposed within a shaft lumen defined by the elongate shaft. The distal end of the pull wire is fixed to the ring and the proximal end of the pull wire is fixed to a slider. The slider is disposed in sliding engagement with a hub that is disposed about a proximal end of the elongate shaft. In a preferred embodiment, the slider and the pull wire may be used to selectively collapse the longitudinally collapsible portion of the elongate shaft. The collapsible portion of the elongate shaft is preferably collapsed by urging the slider proximally relative to the hub. In a preferred method, the guidewire is held stationary relative to the slider, while the slider is moved proximally.

A filter retrieval system in accordance with an exemplary embodiment of the present invention includes a retrieval catheter which may be utilized to retrieve a filter that was previously delivered to a target location in a blood vessel. The filter may be delivered to the target location, for example, using a filter delivery system in accordance with an exemplary embodiment of the present invention.

During a retrieval procedure, the retrieval catheter may be advanced along the guidewire until a distal end of the catheter is proximate the filter. In a preferred embodiment, the catheter includes an elongate shaft and a cone disposed at a distal end of the elongate shaft. The cone preferably has a generally tapered shape that may aid in advancing the catheter through the blood vessel. Also in a preferred embodiment, the cone comprises a flexible material, allowing the cone to deflect as the filter is drawn through an aperture defined by the cone. Embodiments of the cone are possible in which the cone is adapted to fold proximally. Embodiments of the cone are also possible in which the aperture of the cone is adapted to expand radially as the filter passes through the aperture. The distal end of the catheter may be advanced distally relative to the guidewire so that the filter is disposed within a shaft lumen of the catheter.

An additional exemplary embodiment of a filter retrieval system in accordance with the present invention includes a catheter having an elongate shaft and a hub disposed about the elongate shaft proximate the proximal end thereof. A slider is disposed in sliding engagement with a cavity of the hub. The slider includes a wire lock having a plurality of jaws. The wire lock may be used to selectively fix a proximal portion of a guidewire to the slider. A distal end of the guidewire is preferably fixed to a filter which is disposed within a blood vessel.

During a filter retrieval procedure, the hub and the elongate shaft of the catheter may be moved distally relative to the slider and the guidewire. During the movement of the elongate shaft, the longitudinal position of the filter is preferably fixed by the guidewire, since the proximal portion of the guidewire is fixed to the slider by the wire lock. As the catheter is advanced distally, it preferably engulfs the filter. The sliding relationship between the slider and the hub gives the user of the system a defined distance to move the slider relative to the hub when retrieving the filter.

Yet another exemplary embodiment of a filter retrieval system in accordance with the present invention includes a catheter having an elongate shaft including a proximal portion, a distal portion, and a longitudinally expandable portion disposed between the proximal portion and the distal portion. A ring is fixed to the distal portion of the elongate shaft distally of the expandable portion. A push rod is disposed within a shaft lumen defined by the elongate shaft. The distal end of the push rod is fixed to the ring and the proximal end of the push rod is fixed to a slider. The slider is disposed in sliding engagement with a hub that is disposed about a proximal end of the elongate shaft. In a preferred embodiment, the slider and the push rod may be used to selectively expand the longitudinally expandable portion of the elongate shaft. The expandable portion of the elongate shaft is preferably expanded by urging the slider distally relative to the hub. In a preferred method, the guidewire is held stationary relative to the slider, while the slider is moved distally. When this is the case, the filter is preferably engulfed by the distal portion of the catheter.

DETAILED DESCRIPTION OF THE INVENTION

The following detailed description should be read with reference to the drawings, in which like elements in different drawings are numbered in like fashion. The drawings which are not necessarily to scale, depict selected embodiments and are not intended to limit the scope of the invention. In some cases, the drawings may be highly diagrammatic in nature. Examples of constructions, materials, dimensions, and manufacturing processes are provided for various elements. Those skilled in the art will recognize that many of the examples provided have suitable alternatives which may be utilized.

Figure 1:
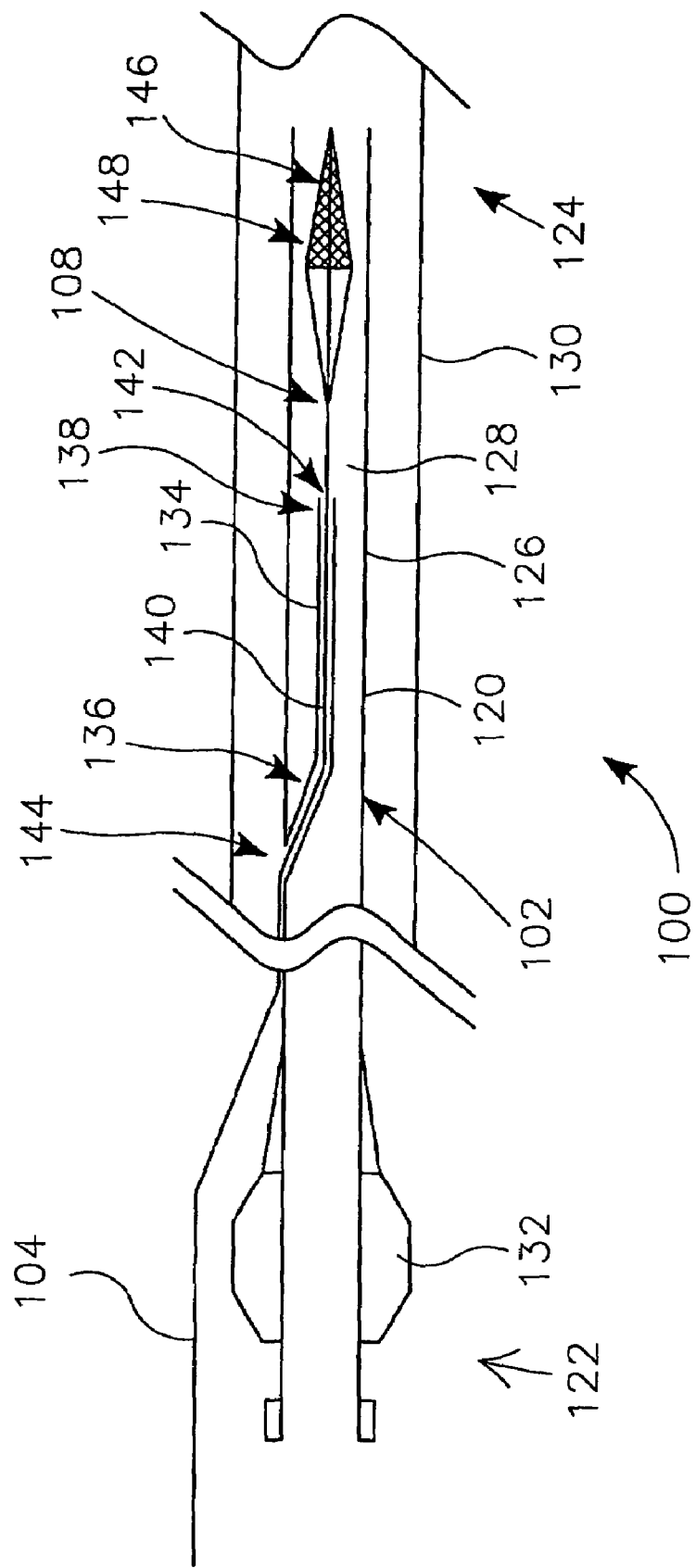
FIG. 1 is a partial cross-sectional view of a filter delivery system in accordance with an exemplary embodiment of the present invention.

FIG. 1 is a partial cross-sectional view of a filter delivery system 100 in accordance with an exemplary embodiment of the present invention. Filter delivery system 100 includes a catheter 102 having an elongate shaft 120. Elongate shaft 120 includes a proximal end 122, a distal end 124, and a wall 126 defining a shaft lumen 128. In the embodiment of FIG. 1, the distal portion of catheter 102 is disposed within a blood vessel 130. In a preferred embodiment, catheter 102 extends out of blood vessel 130, and proximal end 122 of elongate shaft 120 is disposed outside the patient's body. A hub 132 is disposed about elongate shaft 120 proximate proximal end 122.

Catheter 102 also includes a tubular member 134 having a first end 136 fixed to wall 126 of elongate shaft 120, and a second end 138 disposed within shaft lumen 128. Tubular member 134 defines a guidewire lumen 140 which is in fluid communication with a distal guidewire port 142 defined by second end 138 of tubular member 134. Catheter 102 also includes a proximal guidewire port 144 extending through wall 126 of elongate shaft 120. Various embodiments of proximal guidewire port 144 are possible without deviating from the spirit and scope of the present invention. For example, proximal guidewire port 144 may be defined by wall 126 of elongate shaft 120. By way of a second example, proximal guidewire port 144 may be defined by first end 136 of tubular member 134.

In the embodiment of FIG. 1, distal guidewire port 142 is disposed proximally of distal end 124 of elongate shaft 120, and proximal guidewire port 144 is disposed proximally of distal guidewire port 142. In FIG. 1, it may be appreciated that distal guidewire port 142 and proximal guidewire port 144 are separated by a longitudinal distance. In a preferred embodiment, the longitudinal distance between proximal guidewire port 144 and distal guidewire port 142 is less than about 55 centimeters and the length of elongate shaft 120 is between about 100 centimeters and about 300 centimeters. In a more preferred embodiment, the longitudinal distance between proximal guidewire port 144 and distal guidewire port 142 is less than about 45 centimeters. In a particularly preferred embodiment, the longitudinal distance between proximal guidewire port 144 and distal guidewire port 142 is less than about 35 centimeters.

In FIG. 1, it may be appreciated that system 100 includes a filter 146 disposed within a distal portion 148 of shaft lumen 128. In the embodiment of FIG. 1, filter 146 is in a contracted configuration. System 100 of FIG. 1 also includes a guidewire 104 having a distal end 108 that is fixed to filter 146. In the embodiment of FIG. 1, guidewire 104 extends through distal guidewire port 142, guidewire lumen 140, and proximal guidewire port 144.

Figure 2:
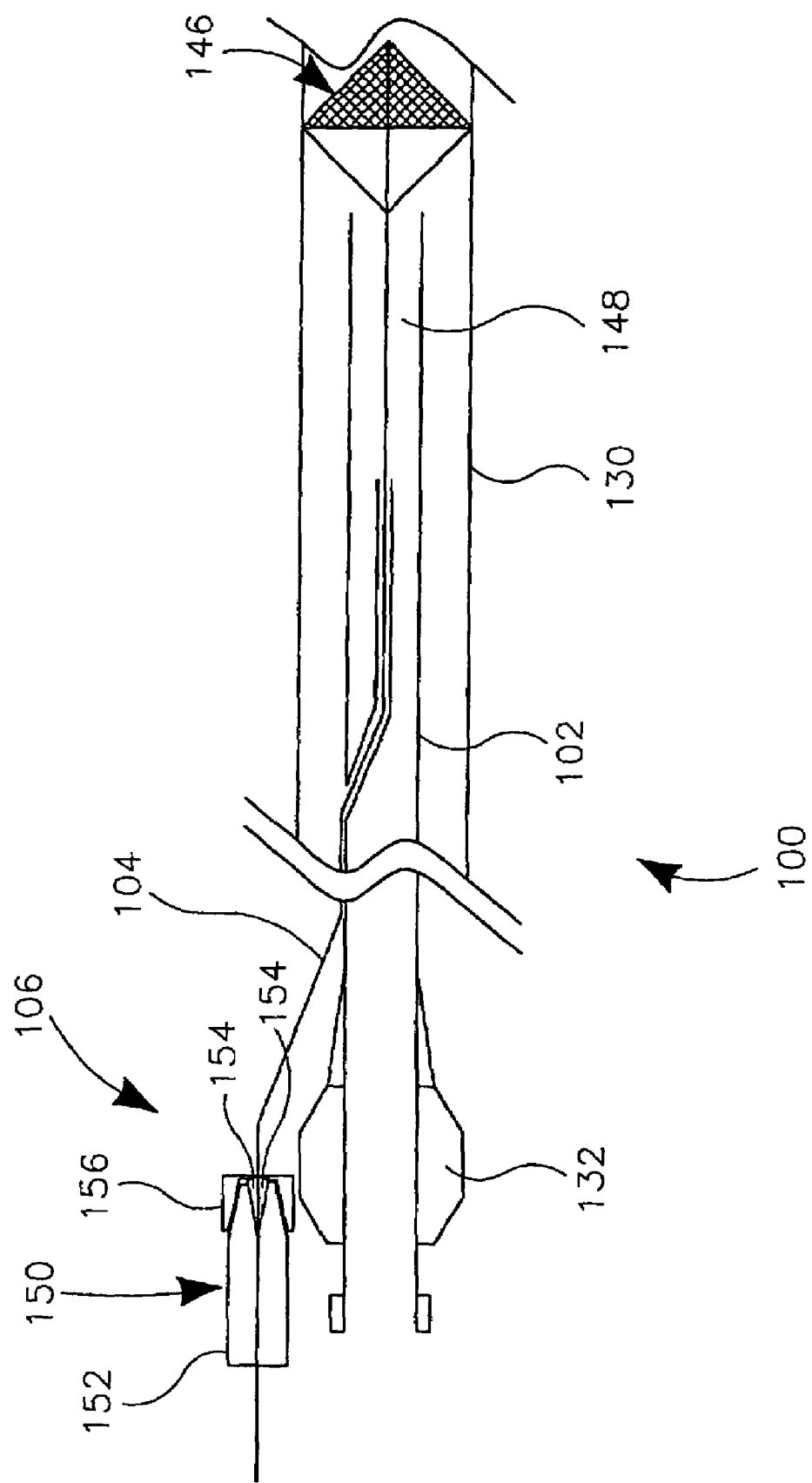
FIG. 2 is a partial cross-sectional view of the filter delivery system of FIG. 1.

FIG. 2 is a partial cross-sectional view of the filter delivery system 100 of FIG. 1. In the embodiment of FIG. 2, catheter 102 has been moved proximally relative to guidewire 104 so that filter 146 is disposed outside of shaft lumen 128. As shown in FIG. 2, filter 146 is free to assume an expanded configuration when it is outside of shaft lumen 128. Catheter 102 may be moved relative to guidewire 104, for example, by grasping a proximal portion 106 of guidewire 104 and applying a pulling force to hub 132 of catheter 102. The pulling force may be applied to hub 132 until filter 146 is deployed in the expanded configuration. The pulling force may also be continued until catheter 102 is removed from blood vessel 130. Once catheter 102 has been removed from blood vessel 130, guidewire 104 may be utilized to guide additional catheters (e.g., balloon catheters, atherectomy catheters, etc.) as they are advanced through blood vessel 130.

In the embodiment of FIG. 2, a wire gripper 150 is disposed about proximal portion 106 of guidewire 104. Wire gripper 150 includes a handle 152 and a plurality of jaws 154 for grasping guidewire 104. A knurl nut fitting 156 is used to selectively urge jaws 154 against guidewire 104. Wire gripper 150 may be used to assist a surgeon in grasping proximal portion 106 of guidewire 104.

Figure 3:
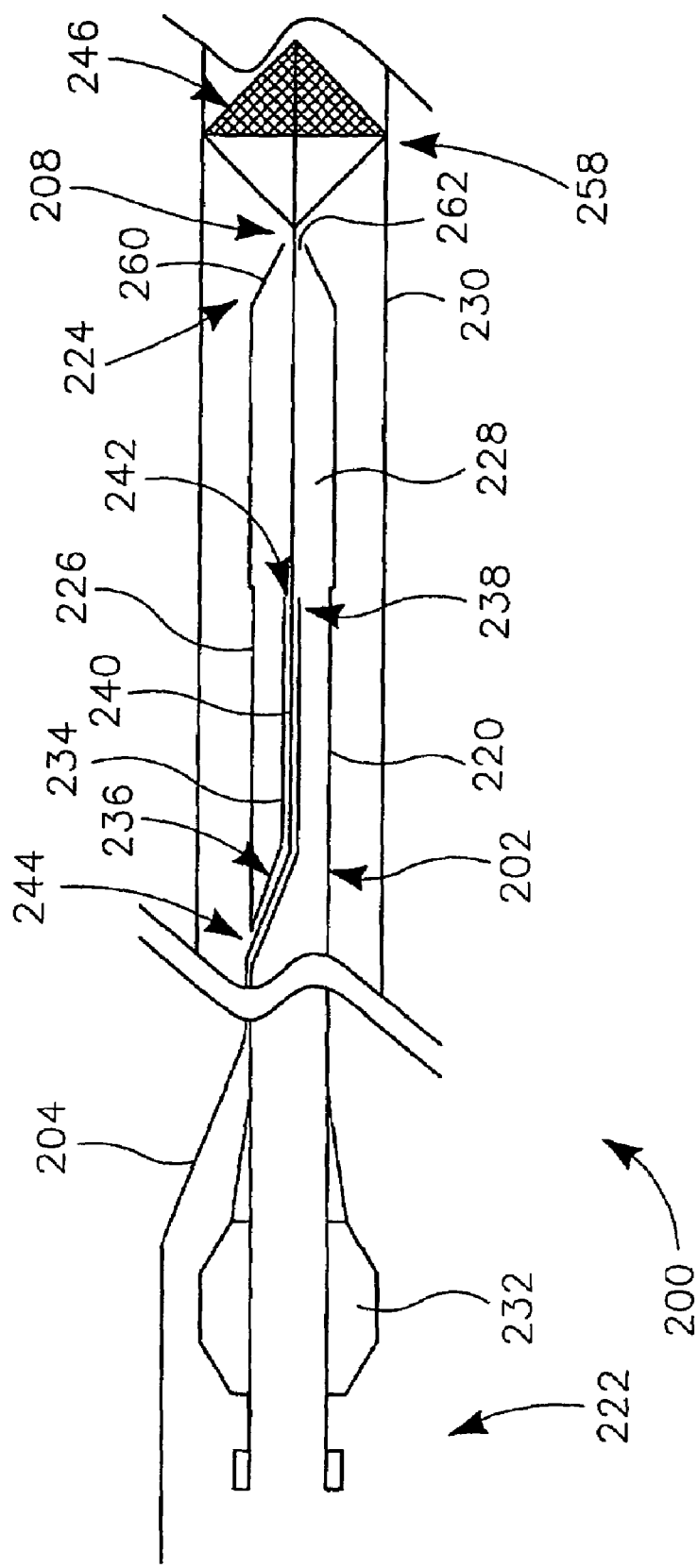
FIG. 3 is a partial cross-sectional view of a filter retrieval system in accordance with an exemplary embodiment of the present invention.

FIG. 3 is a partial cross-sectional view of a filter retrieval system 200 in accordance with an exemplary embodiment of the present invention. Filter retrieval system 200 includes a catheter 202 that may be utilized to retrieve a filter 246 that was previously delivered to a target location 258 in a blood vessel 230. Filter 246 may be delivered to target location, for example, using the filter delivery system of FIG. 1 and FIG. 2, and/or other filter delivery systems in accordance with the present invention. In FIG. 3 it may be appreciated that a distal end 208 of a guidewire 204 is fixed to filter 146.

In the embodiment of FIG. 3, guidewire 204 extends through a distal guidewire port 242, and a guidewire lumen 240 defined by a tubular member 234 of catheter 202. In the embodiment of FIG. 3, a first end 236 of tubular member 234 is fixed to a wall 226 of elongate shaft 220 of catheter 202. A second end 238 of tubular member 234 is disposed within a shaft lumen 228 defined by wall 226 of elongate shaft 220.

Guidewire 204 also extends through a proximal guidewire port 244 extending through wall 226 of elongate shaft 220. Various embodiments of proximal guidewire port 244 are possible without deviating from the spirit and scope of the present invention. For example, proximal guidewire port 244 may be defined by wall 226 of elongate shaft 220. By way of a second example, proximal guidewire port 244 may be defined by first end 236 of tubular member 234.

In the embodiment of FIG. 3, catheter 202 has been advanced along guidewire 204 until a distal end 224 of elongate shaft 220 is proximate filter 246. In FIG. 3, it may be appreciated that a cone 260 is disposed at distal end 224 of elongate shaft 220. The generally tapered shape of cone 260 may aid in advancing catheter 202 through blood vessel 230. In a preferred embodiment, cone 260 comprises a flexible material, allowing cone 260 to deflect as filter 246 is drawn through an aperture 262 defined by cone 260. Embodiments of cone 260 are possible in which cone 260 is adapted to fold proximally as filter 246 passes through aperture 262. Embodiments of cone 260 are also possible in which cone 260 is adapted to expand radially as filter 246 passes through aperture 262.

In a preferred embodiment, catheter 202 extends out of blood vessel 230, so that a proximal end 222 of elongate shaft 220 is disposed outside the patient's body. As shown in FIG. 3, a hub 232 is disposed about elongate shaft 220 proximate proximal end 222. Hub 232 may aid a surgeon in grasping elongate shaft 220.

In the embodiment of FIG. 3, distal guidewire port 242 is disposed proximally of distal end 224 of elongate shaft 220, and proximal guidewire port 244 is disposed proximally of distal guidewire port 242. In FIG. 3, it may be appreciated that distal guidewire port 242 and proximal guidewire port 244 are separated by a longitudinal distance. In a preferred embodiment, the longitudinal distance between proximal guidewire port 244 and distal guidewire port 242 is less than about 55 centimeters. In a more preferred embodiment, the longitudinal distance between proximal guidewire port 244 and distal guidewire port 242 is less than about 45 centimeters. In a particularly preferred embodiment, the longitudinal distance between proximal guidewire port 244 and distal guidewire port 242 is less than about 35 centimeters. In FIG. 3, it may be appreciated that filter 246 is disposed within blood vessel 230 in an expanded configuration.

Figure 4:
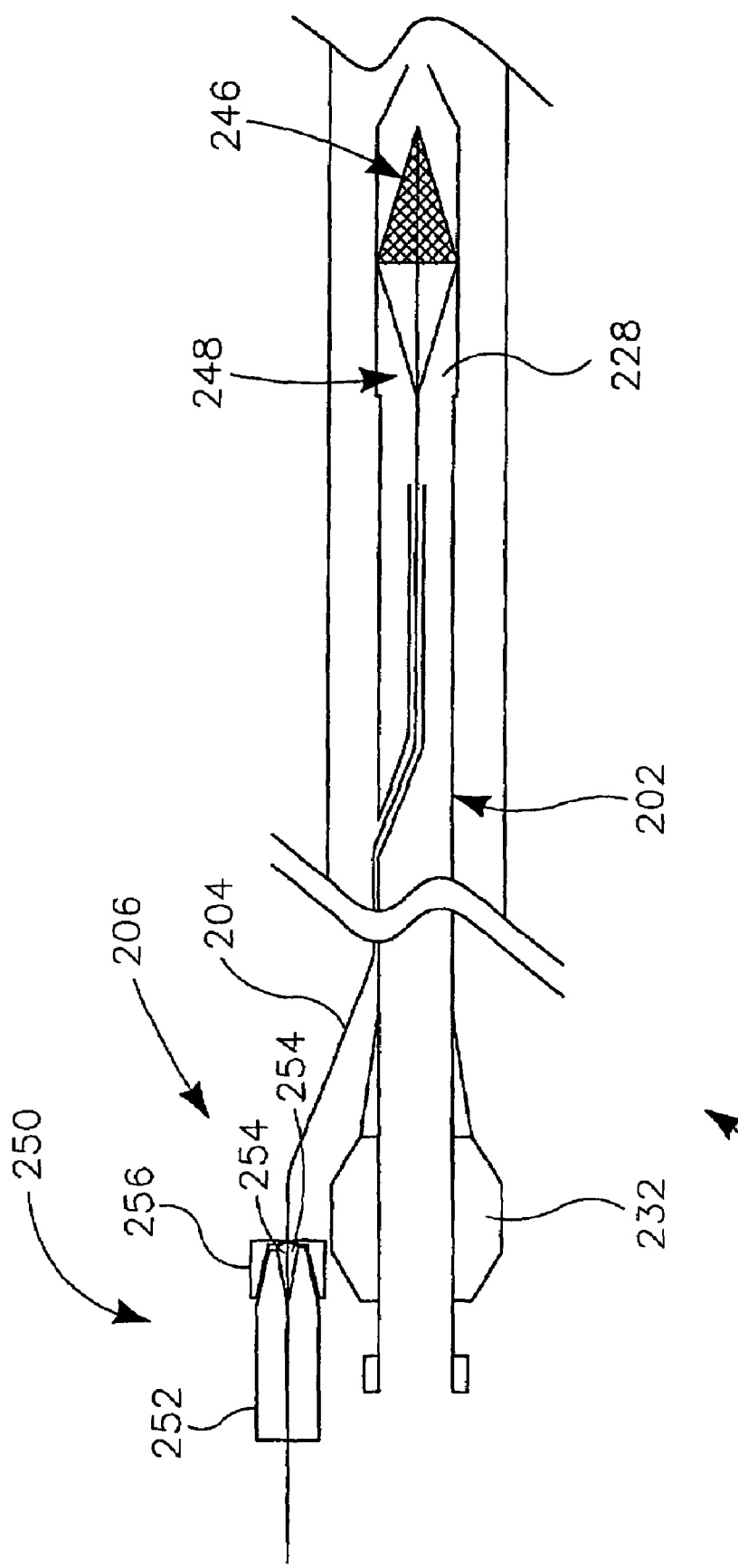
FIG. 4 is a partial cross-sectional view of the filter retrieval system of FIG. 3.

FIG. 4 is a partial cross-sectional view of the filter retrieval system 200 of FIG. 3. In the embodiment of FIG. 4, catheter 202 has been advanced distally relative to guidewire 204 so that filter 246 is disposed within a distal portion 248 of shaft lumen 228. As shown in FIG. 4, filter 246 has been urged into a contracted configuration. Catheter 202 may be moved relative to guidewire 204, for example, by grasping a proximal portion 206 of guidewire 204 and applying a pushing force to hub 232.

In the embodiment of FIG. 4, a wire gripper 250 is disposed about proximal portion 206 of guidewire 204. Wire gripper 250 includes a handle 252 and a plurality of jaws 254 for grasping guidewire 204. A knurl nut fitting 256 is used to selectively urge jaws 254 against guidewire 204. Wire gripper 250 may be used to assist a surgeon in grasping proximal portion 206 of guidewire 204.

Figure 5:
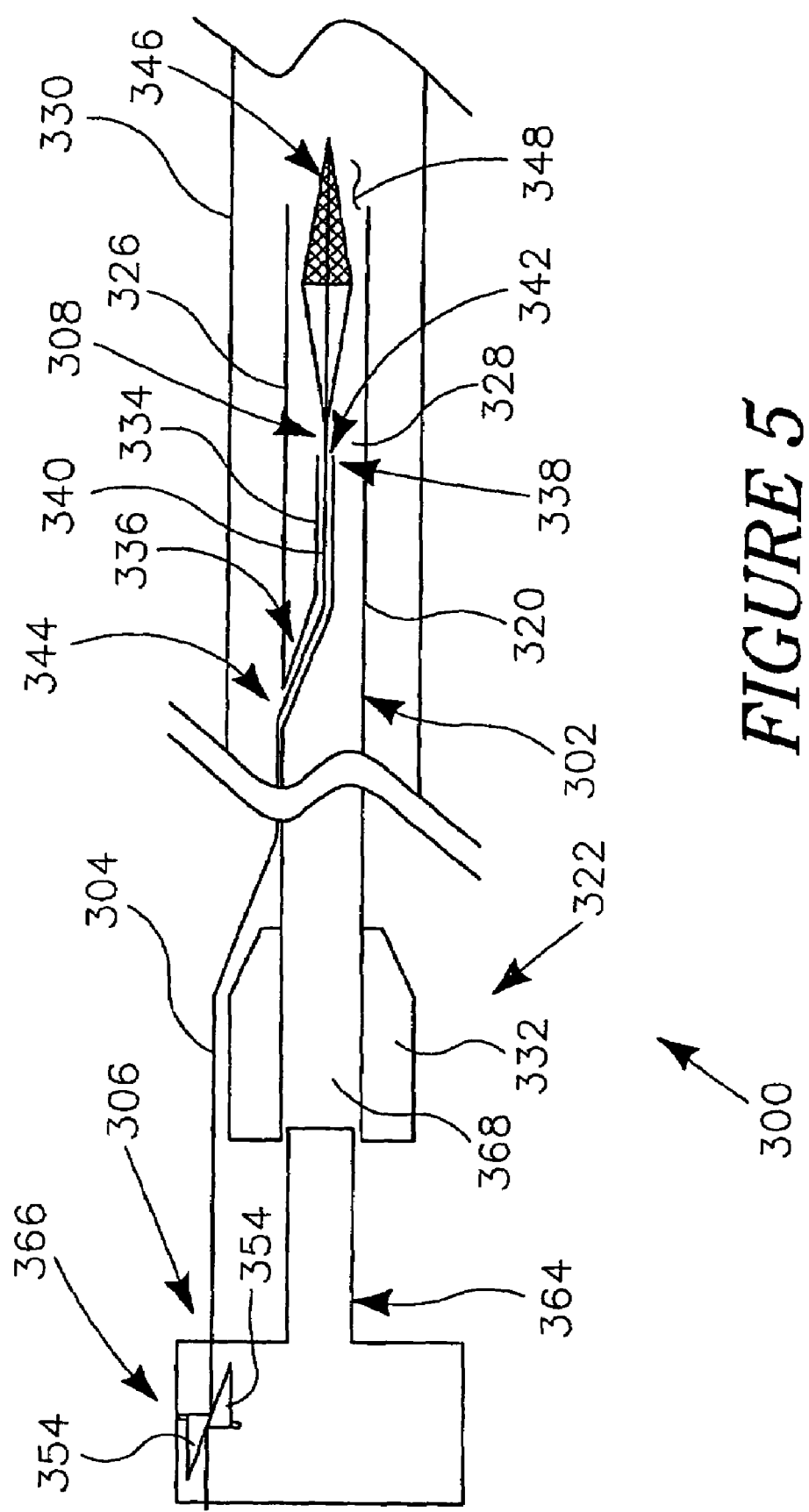
FIG. 5 is a partial cross-sectional view of a filter delivery system in accordance with an additional exemplary embodiment of the present invention.

FIG. 5 is a partial cross-sectional view of a filter delivery system 300 in accordance with an additional exemplary embodiment of the present invention. Filter delivery system 300 includes a catheter 302 having an elongate shaft 320. A hub 332 is disposed about elongate shaft 320 proximate proximal end 322 thereof. A slider 364 is disposed in sliding engagement with a cavity 368 of hub 332. Slider 364 includes a wire lock 366 having a plurality of jaws 354. Wire lock 366 may be used to selectively fix a proximal portion 306 of a guidewire 304 to slider 364.

Guidewire 304 extends distally away from wire lock 366. As shown in FIG. 5, a portion of guidewire 304 is disposed in a guidewire lumen 340 defined by a tubular member 334. A first end 336 of tubular member 334 is fixed to a wall 326 of elongate shaft 320, and a second end 338 of tubular member 334 is disposed within a shaft lumen 328 defined by wall 326. Guidewire lumen 340 is in fluid communication with a distal guidewire port 342 defined by second end 338 of tubular member 334. Catheter 302 also includes a proximal guidewire port 344 extending through wall 326 of elongate shaft 320.

In FIG. 5, it may be appreciated that a distal end 308 of guidewire 304 is fixed to a filter 346 that is disposed within a distal portion 348 of shaft lumen 328. In the embodiment of FIG. 5, filter 346 is in a contracted configuration. System 300 may be utilized to deploy filter 346 into a blood vessel 330 as shown in FIG. 6.

Figure 6:
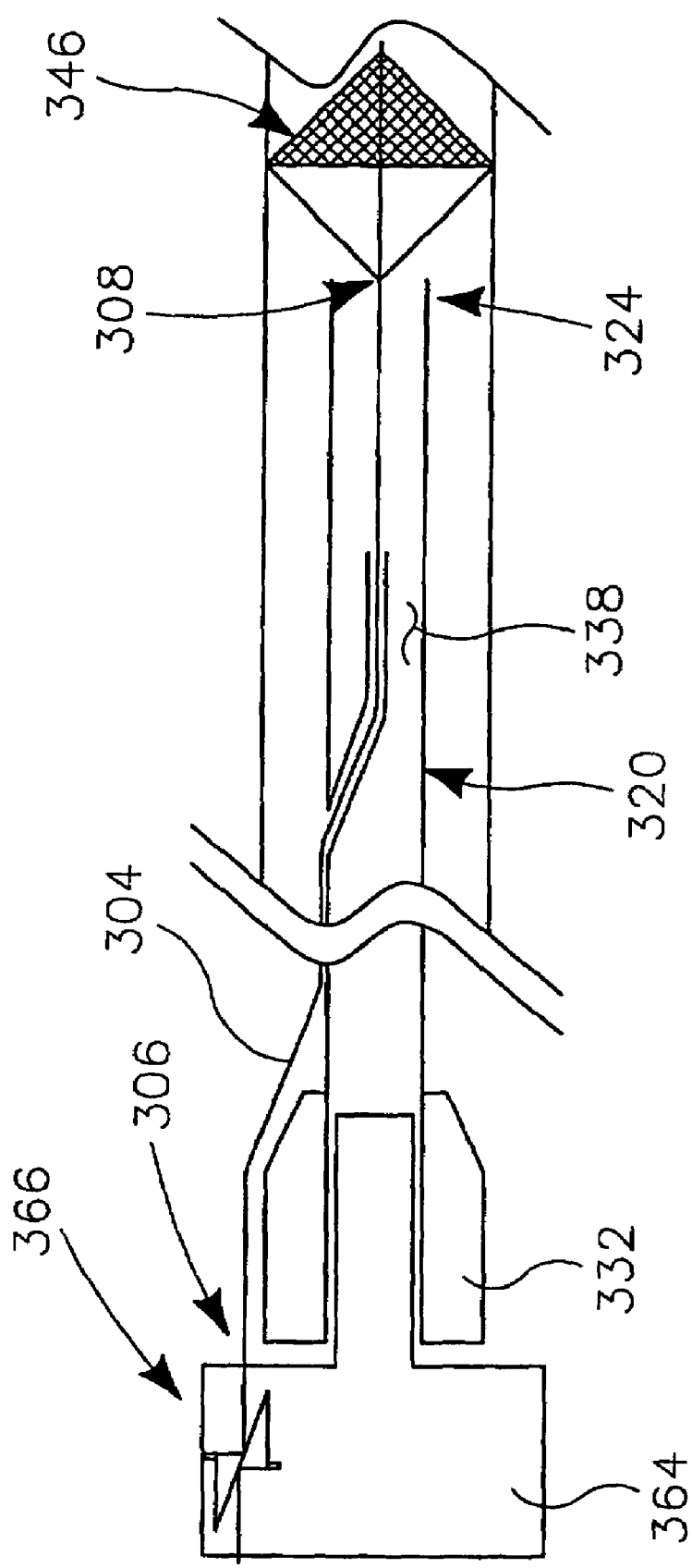
FIG. 6 is a partial cross-sectional view of the filter delivery system of FIG. 5.

FIG. 6 is a partial cross-sectional view of the filter retrieval system 300 of FIG. 5. In the embodiment of FIG. 6, hub 332 of catheter 302 has been moved proximally relative to slider 364. As described previously, proximal portion 306 of guidewire 304 is fixed to slider 364 by wire lock 366, and filter 346 is fixed to distal end 308 of guidewire 304. Thus, when hub 332 is moved proximally relative to slider 364, distal end 324 of elongate shaft 320 is urged proximally so that filter 346 is disposed outside of shaft lumen 328 of elongate shaft 320. Once filter 346 is out of shaft lumen 328 it is free to assume an expanded configuration as shown in FIG. 6. The sliding relationship between slider 364 and hub 332 gives the user of system 300 a defined distance to move slider 364 relative to hub 332 when deploying filter 346.

Figure 7:
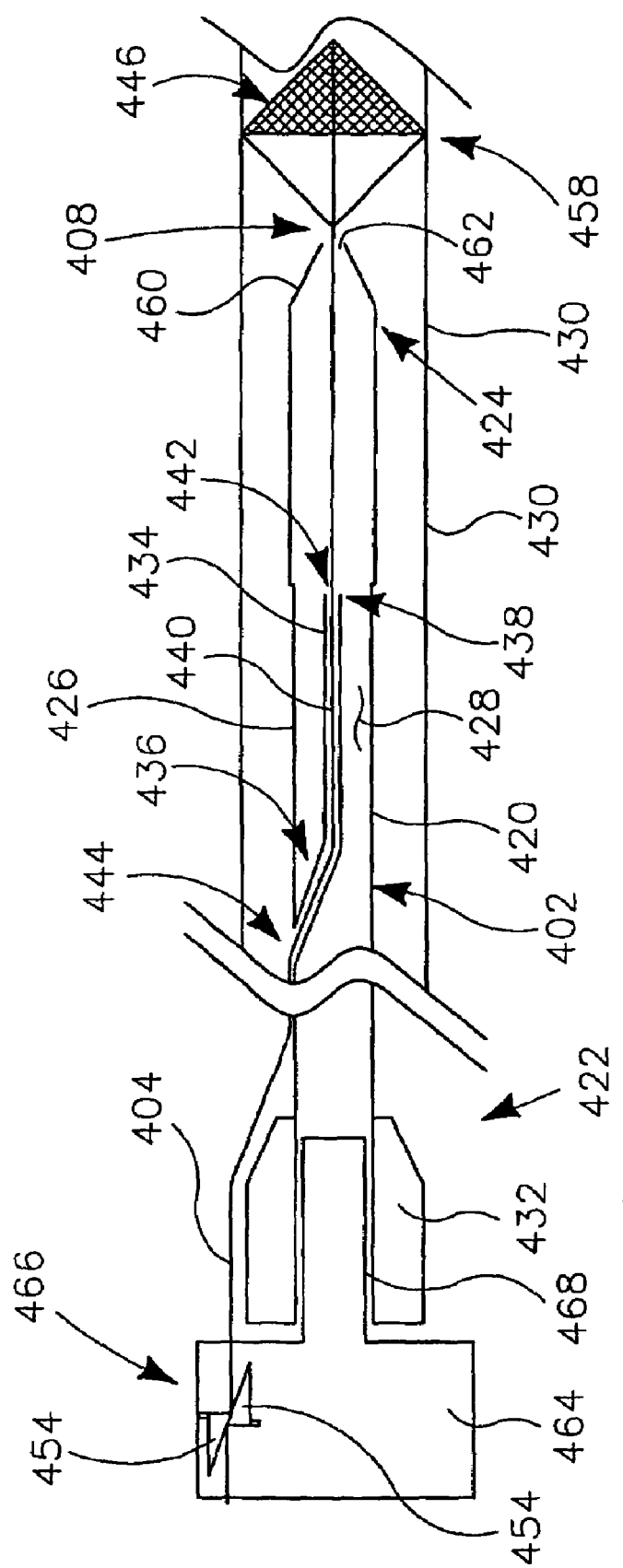
FIG. 7 is a partial cross-sectional view of a filter retrieval system in accordance with an additional exemplary embodiment of the present invention.

FIG. 7 is a partial cross-sectional view of a filter retrieval system 400 in accordance with an exemplary embodiment of the present invention. Filter retrieval system 400 includes a catheter 402 that may be utilized to retrieve a filter 446 that was previously delivered to a target location 458 in a blood vessel 430.

In the embodiment of FIG. 7, a distal end 408 of a guidewire 404 is fixed filter 446. Guidewire 404 extends proximally away from filter 446 passing through a distal guidewire port 442, and a guidewire lumen 440 defined by a tubular member 434 of catheter 402. In the embodiment of FIG. 7, a first end 436 of tubular member 434 is fixed to a wall 426 of an elongate shaft 420 of catheter 402. A second end 438 of tubular member 434 is disposed within a shaft lumen 428 defined by wall 426 of elongate shaft 420.

Guidewire 404 also extends through a proximal guidewire port 444 extending through wall 426 of elongate shaft 420. Various embodiments of proximal guidewire port 444 are possible without deviating from the spirit and scope of the present invention. For example, proximal guidewire port 444 may be defined by wall 426 of elongate shaft 420. By way of a second example, proximal guidewire port 444 may be defined by first end 436 of tubular member 434.

In the embodiment of FIG. 7, catheter 402 has been advanced along guidewire 404 until a distal end 424 of elongate shaft 420 is proximate filter 446. In FIG. 7, it may be appreciated that a cone 460 is disposed at distal end 424 of elongate shaft 420. The generally tapered shape of cone 460 may aid in advancing catheter 402 through blood vessel 430. In a preferred embodiment, cone 460 comprises a flexible material, allowing cone 460 to deflect as filter 446 is drawn through an aperture 462 defined by cone 460. Embodiments of cone 460 are possible in which cone 460 is adapted to fold proximally as filter 446 passes through aperture 462. Embodiments of cone 460 are also possible in which cone 460 is adapted to expand radially as filter 446 passes through aperture 462.

In a preferred embodiment, catheter 402 extends out of blood vessel 430, so that a proximal end 422 of elongate shaft 420 is disposed outside the patient's body. As shown in FIG. 7, a hub 432 is disposed about elongate shaft 420 proximate proximal end 422. A slider 464 is disposed in sliding engagement with a cavity 468 of hub 432. Slider 464 includes a wire lock 466 having a plurality of jaws 454. Wire lock 466 may be used to selectively fix a proximal portion 406 of guidewire 404 to slider 464. System 400 may be utilized to retrieve filter 446 from blood vessel 430 as shown in FIG. 8.

Figure 8:
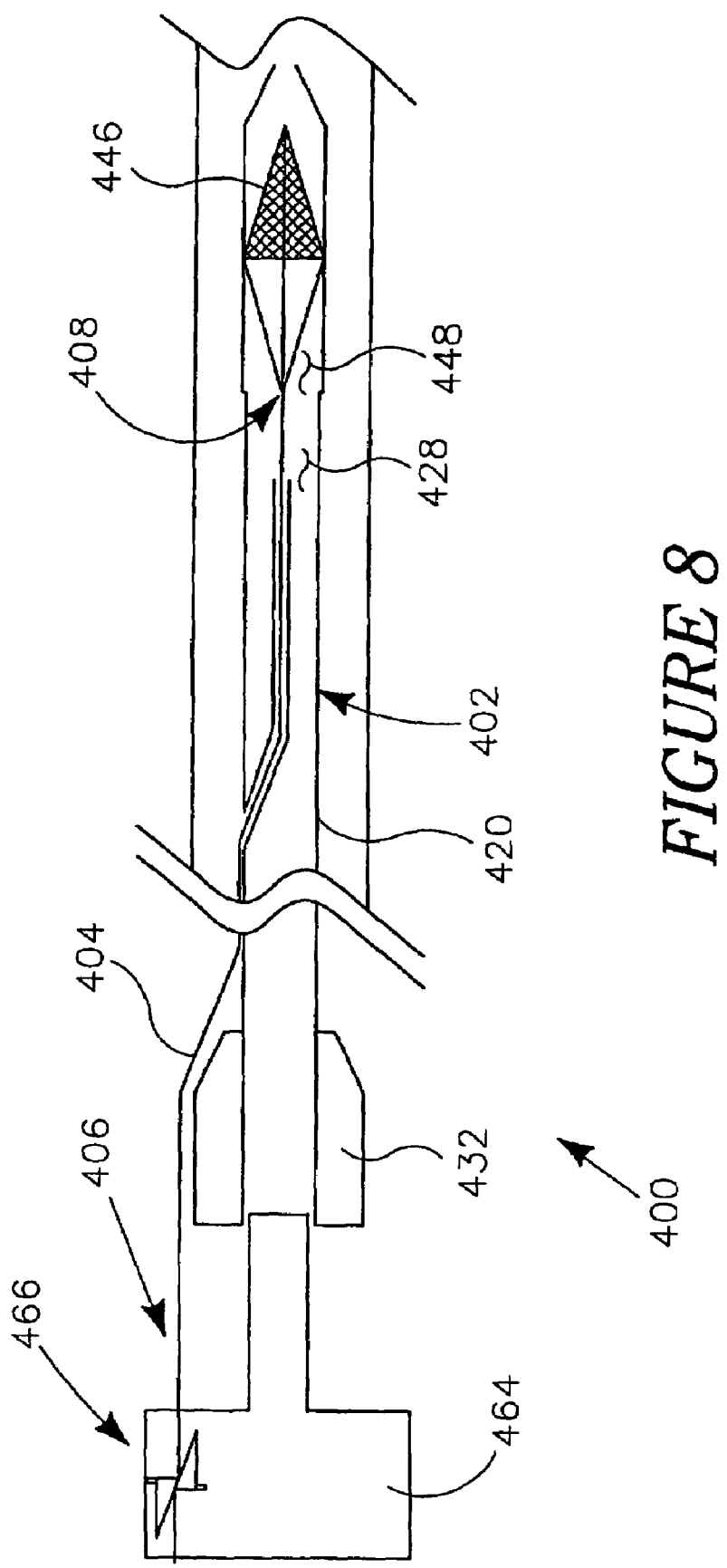
FIG. 8 is a partial cross-sectional view of the filter retrieval system of FIG. 7.

FIG. 8 is a partial cross-sectional view of the filter retrieval system 400 of FIG. 7. In the embodiment of FIG. 8, hub 432 and elongate shaft 420 of catheter 402 have been moved distally relative to slider 464. During the movement of elongate shaft 420, the longitudinal position of filter 446 is fixed by guidewire 404, since proximal portion 406 of guidewire 404 is fixed to slider 464 by wire lock 466 and distal end 408 of guidewire 404 is fixed to filter 446.

As elongate shaft 420 is advanced distally, it engulfs filter 446. In the embodiment of FIG. 8 filter 446 is disposed within a distal portion 448 of shaft lumen 428. As shown in FIG. 8, filter 446 is urged into a contracted configuration when it is disposed within shaft lumen 428. The sliding relationship between slider 464 and hub 432 gives the user of system 400 a defined distance to move slider 464 relative to hub 432 when retrieving filter 446.

Figure 9:
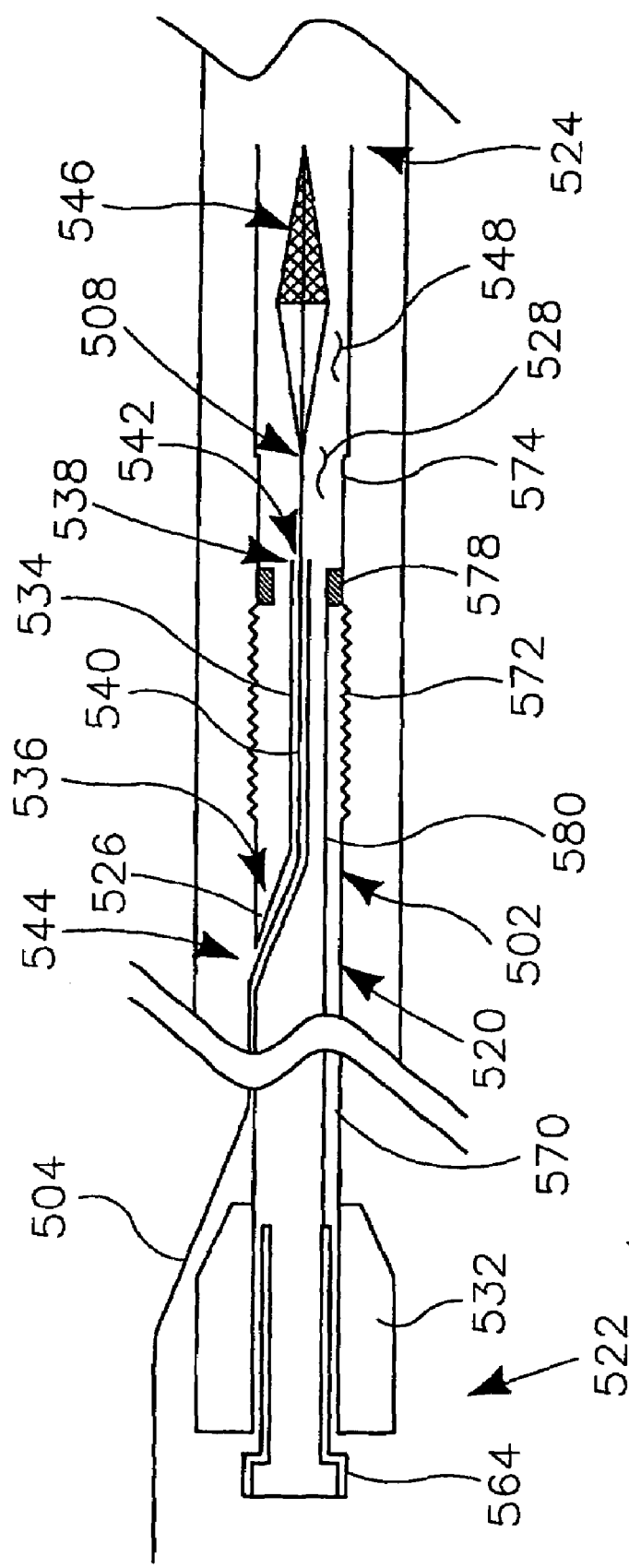
FIG. 9 is a partial cross-sectional view of a filter delivery system in accordance with an additional exemplary embodiment of the present invention.

FIG. 9 is a partial cross-sectional view of a filter delivery system 500 in accordance with yet another exemplary embodiment of the present invention. Filter delivery system 500 includes a catheter 502 having an elongate shaft 520. Elongate shaft 520 includes a proximal portion 570, a distal portion 574, and a longitudinally collapsible portion 572 disposed between proximal portion 570 and distal portion 574.

A ring 578 is fixed to distal portion 574 of elongate shaft 520 distally of collapsible portion 572. A pull wire 580 is disposed within a shaft lumen 528 defined by elongate shaft 520. The distal end of pull wire 580 is fixed to ring 578 and the proximal end of pull wire 580 is fixed to a slider 564. Slider 564 is disposed in sliding engagement with a hub 532 which is disposed about a proximal end 522 of elongate shaft 520. In a preferred embodiment, slider 564 and pull wire 580 may be used to selectively collapse longitudinally collapsible portion 572 of elongate shaft 520.

Catheter 502 also includes a tubular member 534 having a first end 536 fixed to a wall 526 of proximal portion 570 of elongate shaft 520, and a second end 538 disposed within shaft lumen 528. Tubular member 534 defines a guidewire lumen 540 which is in fluid communication with a distal guidewire port 542 defined by second end 538 of tubular member 534. Catheter 502 also includes a proximal guidewire port 544 extending through wall 526 of proximal portion 570 of elongate shaft 520. Various embodiments of proximal guidewire port 544 are possible without deviating from the spirit and scope of the present invention. For example, proximal guidewire port 544 may be defined by wall 526 of proximal portion 570 of elongate shaft 520. By way of a second example, proximal guidewire port 544 may be defined by first end 536 of tubular member 534.

In the embodiment of FIG. 9, distal guidewire port 542 is disposed proximally of a distal end 524 of elongate shaft 520, and proximal guidewire port 544 is disposed proximally of distal guidewire port 542. In FIG. 9, it may be appreciated that distal guidewire port 542 and proximal guidewire port 544 are separated by a longitudinal distance. In a preferred embodiment, the longitudinal distance between proximal guidewire port 544 and distal guidewire port 542 is less than about 55 centimeters. In a more preferred embodiment, the longitudinal distance between proximal guidewire port 544 and distal guidewire port 542 is less than about 45 centimeters. In a particularly preferred embodiment, the longitudinal distance between proximal guidewire port 544 and distal guidewire port 542 is less than about 35 centimeters.

In FIG. 9, it may be appreciated that system 500 includes a filter 546 disposed within a distal portion 548 of shaft lumen 528. In the embodiment of FIG. 9, filter 546 is in a contracted configuration. System 500 of FIG. 9 also includes a guidewire 504 having a distal end 508 that is fixed to filter 546. In the embodiment of FIG. 9, guidewire 504 extends through distal guidewire port 542, guidewire lumen 540, and proximal guidewire port 544.

Figure 10:
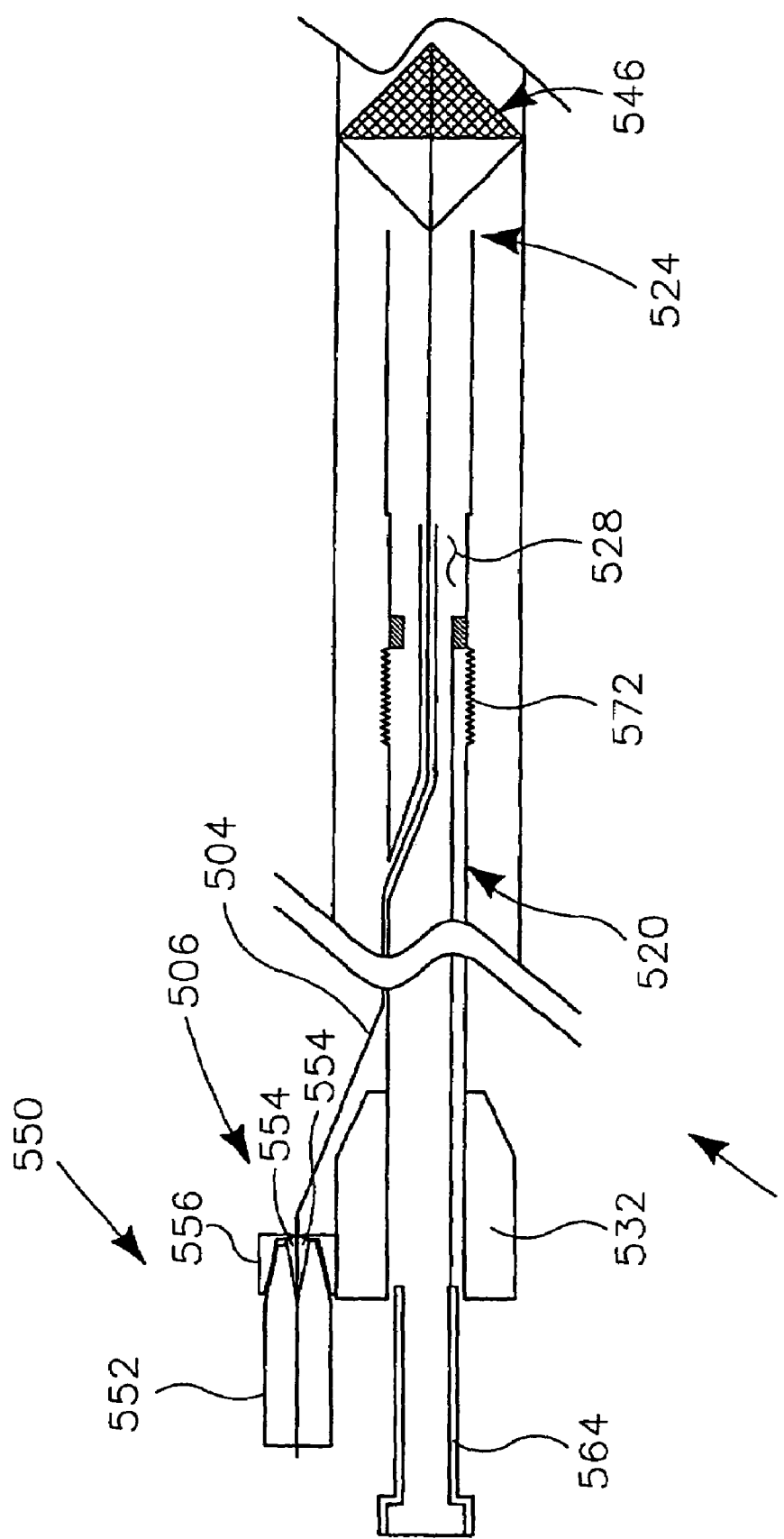
FIG. 10 is a partial cross-sectional view of the filter delivery system of FIG. 9.

FIG. 10 is a partial cross-sectional view of the filter delivery system 500 of FIG. 9. In the embodiment of FIG. 10, longitudinally collapsible portion 572 of elongate shaft 520 has been collapsed by urging slider 564 proximally relative to hub 532. In a preferred method in accordance with the present invention, guidewire 504 is held stationary while slider 564 is moved proximally.

A wire gripper 550 may be used to assist a surgeon grasping a proximal portion 506 of guidewire 504 and holding it stationary. In the embodiment of FIG. 10, wire gripper 550 is disposed about proximal portion 506 of guidewire 504. Wire gripper 550 includes a handle 552 and a plurality of jaws 554 for grasping guidewire 504. A knurl nut fitting 556 is used to selectively urge jaws 554 against guidewire 504.

In the embodiment of FIG. 10, collapsible portion 572 has been collapsed to such an extent that distal end 524 of elongate shaft 520 is located proximally of filter 546 and filter 546 is disposed outside of shaft lumen 528. In FIG. 10 it may be appreciated that filter 546 is free to assume an expanded configuration when it is outside of shaft lumen 528.

Figure 11:
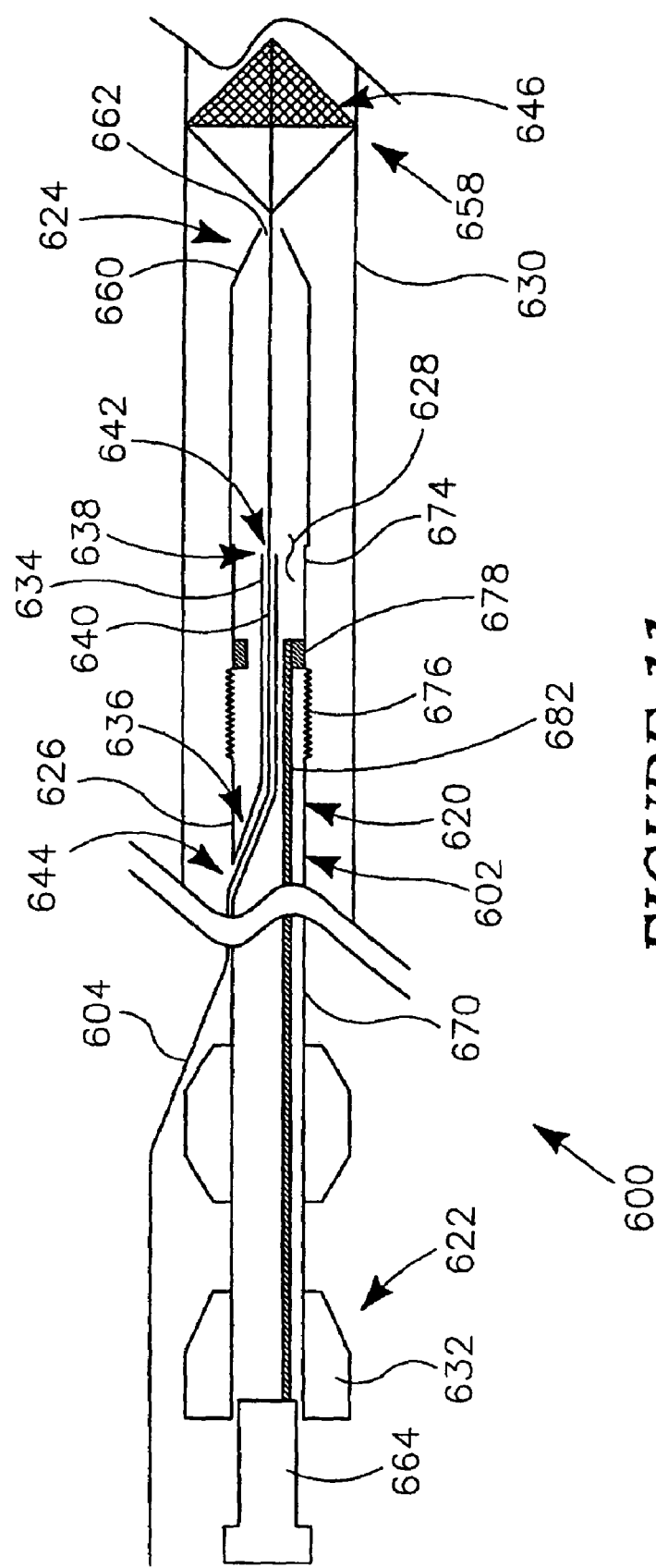
FIG. 11 is a partial cross-sectional view of a filter retrieval system in accordance with an additional exemplary embodiment of the present invention.

FIG. 11 is a partial cross-sectional view of a filter retrieval system 600 in accordance with an exemplary embodiment of the present invention. Filter retrieval system 600 includes a catheter 602 that may be utilized to retrieve a filter 646 that was previously delivered to a target location 658 in a blood vessel 630. Filter 646 may be delivered to a target location, for example, using the filter delivery system of FIG. 9 and FIG. 10, and/or other filter delivery systems in accordance with the present invention.

Catheter 602 of filter retrieval system 600 includes an elongate shaft 620 including a proximal portion 670, a distal portion 674, and a longitudinally expandable portion 676 disposed between proximal portion 670 and distal portion 674. A ring 678 is fixed to distal portion 674 of elongate shaft 620 distally of expandable portion 676. A push rod 682 is disposed within a shaft lumen 628 defined by elongate shaft 620. The distal end of push rod 682 is fixed to ring 678 and the proximal end of push rod 682 is fixed to a slider 664. Slider 664 is disposed in sliding engagement with a hub 632 which is disposed about a proximal end 622 of elongate shaft 620. In a preferred embodiment, slider 664 and push rod 682 may be used to selectively expand longitudinally expandable portion 676 of elongate shaft 620.

In the embodiment of FIG. 11, a guidewire 604 extends through a distal guidewire port 642, and a guidewire lumen 640 defined by a tubular member 634 of catheter 602. In the embodiment of FIG. 11, a first end 636 of tubular member 634 is fixed to a wall 626 of elongate shaft 620 of catheter 602. A second end 638 of tubular member 634 is disposed within shaft lumen 628 of elongate shaft 620. Guidewire 604 also extends through a proximal guidewire port 644 extending through wall 626 of elongate shaft 620. Various embodiments of proximal guidewire port 644 are possible without deviating from the spirit and scope of the present invention. For example, proximal guidewire port 644 may be defined by wall 626 of elongate shaft 620. By way of a second example, proximal guidewire port 644 may be defined by first end 636 of tubular member 634.

In the embodiment of FIG. 11, catheter 602 has been advanced along guidewire 604 until a distal end 624 of elongate shaft 620 is proximate filter 646. In FIG. 11, it may be appreciated that a cone 660 is disposed at distal end 624 of elongate shaft 620. The generally tapered shape of cone 660 may aid in advancing catheter 602 through blood vessel 630. In a preferred embodiment, cone 660 comprises a flexible material, allowing cone 660 to deflect as filter 646 is drawn through an aperture 662 defined by cone 660. Embodiments of cone 660 are possible in which cone 660 is adapted to fold proximally as filter 646 passes through aperture 662. Embodiments of cone 660 are also possible in which cone 660 is adapted to expand radially as filter 646 passes through aperture 662.

In the embodiment of FIG. 11, distal guidewire port 642 is disposed proximally of distal end 624 of elongate shaft 620, and proximal guidewire port 644 is disposed proximally of distal guidewire port 642. In FIG. 11, it may be appreciated that distal guidewire port 642 and proximal guidewire port 644 are separated by a longitudinal distance. In a preferred embodiment, the longitudinal distance between proximal guidewire port 644 and distal guidewire port 642 is less than about 55 centimeters. In a more preferred embodiment, the longitudinal distance between proximal guidewire port 644 and distal guidewire port 642 is less than about 45 centimeters. In a particularly preferred embodiment, the longitudinal distance between proximal guidewire port 644 and distal guidewire port 642 is less than about 35 centimeters. In FIG. 11, it may be appreciated that filter 646 is disposed within blood vessel 630 in an expanded configuration.

Figure 12:
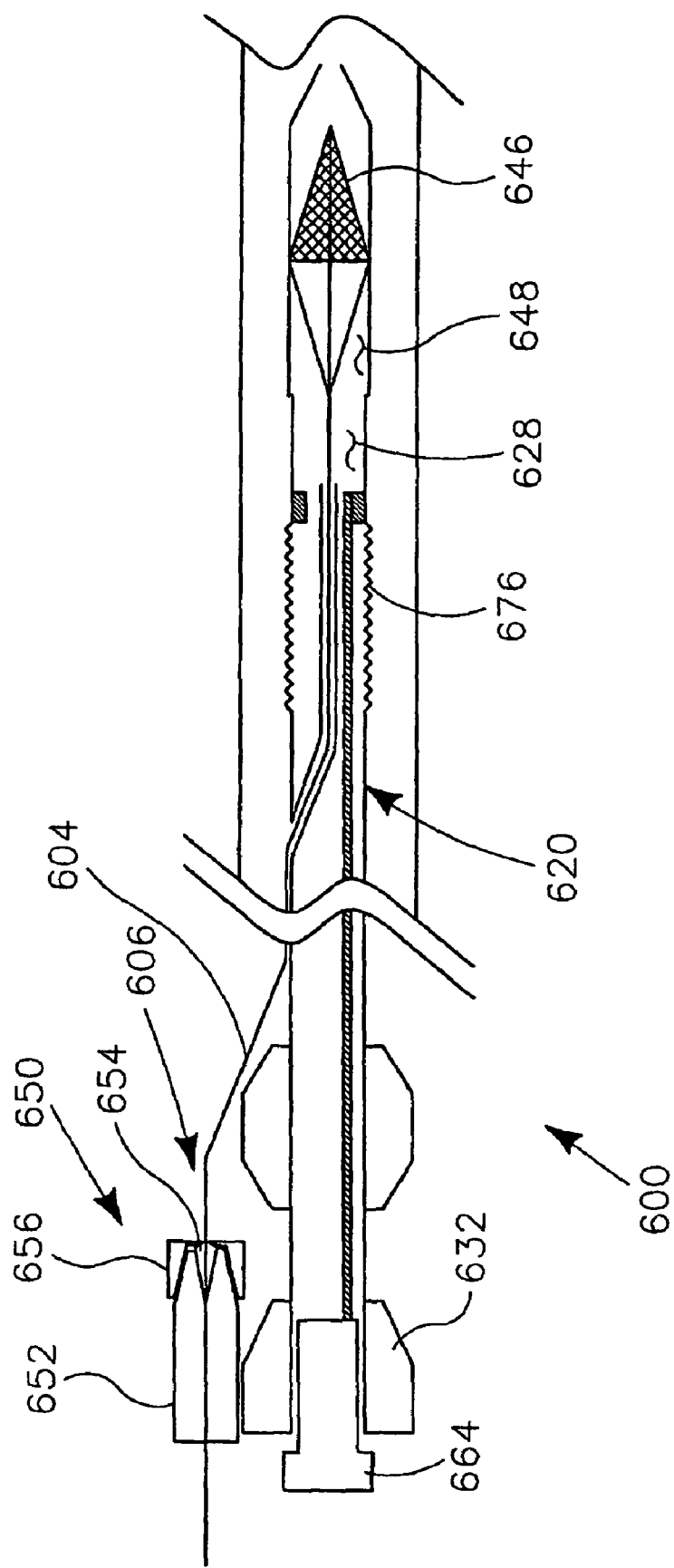
FIG. 12 is a partial cross-sectional view of the filter retrieval system of FIG. 11.

FIG. 12 is a partial cross-sectional view of the filter retrieval system 600 of FIG. 11. In the embodiment of FIG. 12, expandable portion 676 of elongate shaft 620 has been expanded so that filter 646 is disposed within a distal portion 648 of shaft lumen 628. Expandable portion 676 of elongate shaft 620 may be expanded, for example, by urging slider 664 distally relative to hub 632. As shown in FIG. 12, filter 646 has been urged into a contracted configuration.

In a preferred method in accordance with the present invention, guidewire 604 is held in place while selectively expandable portion 676 is expanded, for example, by grasping a proximal portion 606 of guidewire 604. In the embodiment of FIG. 12, a wire gripper 650 is disposed about proximal portion 606 of guidewire 604. Wire gripper 650 includes a handle 652 and a plurality of jaws 654 for grasping guidewire 604. A knurl nut fitting 656 is used to selectively urge jaws 654 against guidewire 604. Wire gripper 650 may be used to assist a surgeon in grasping proximal portion 606 of guidewire 604.

Figure 13:
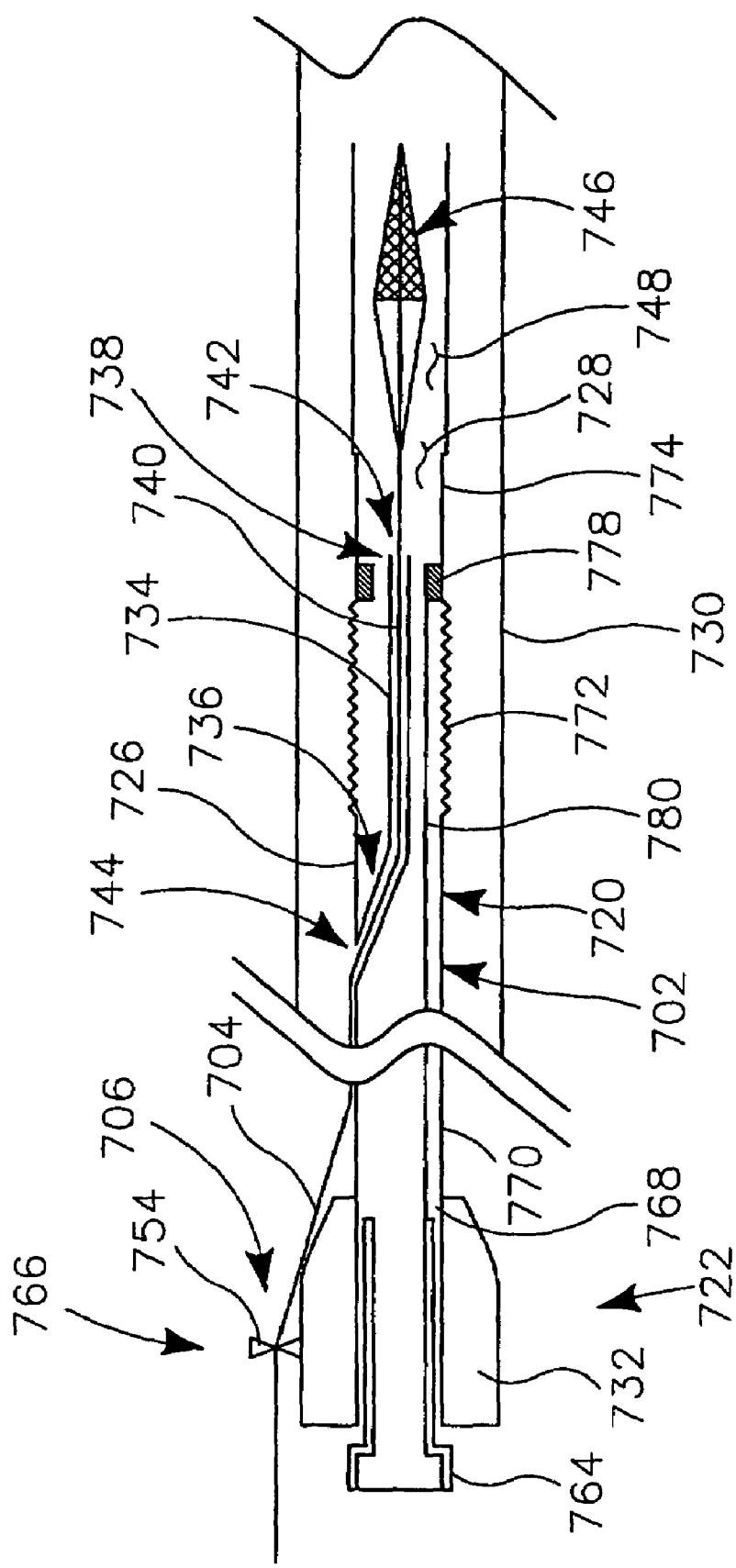
FIG. 13 is a partial cross-sectional view of a filter delivery system in accordance with an additional exemplary embodiment of the present invention.

FIG. 13 is a partial cross-sectional view of a filter delivery system 700 in accordance with an additional exemplary embodiment of the present invention. Filter delivery system 700 includes a catheter 702 having an elongate shaft 720 having a proximal end 722. A hub 732 is disposed about elongate shaft 720 proximate proximal end 722. A slider 764 is disposed in sliding engagement with a cavity 768 of hub 732. Hub 732 includes a wire lock 766 having a plurality of jaws 754. Wire lock 766 may be used to selectively fix a proximal portion 706 of a guidewire 704 to hub 732.

Elongate shaft 720 includes a proximal portion 770, a distal portion 774, and a longitudinally collapsible portion 772 disposed between proximal portion 770 and distal portion 774. A ring 778 is fixed to distal portion 774 of elongate shaft 720 distally of collapsible portion 772. A pull wire 780 is disposed within a shaft lumen 728 defined by elongate shaft 720. The distal end of pull wire 780 is fixed to ring 778 and the proximal end of pull wire 780 is fixed to slider 764. In a preferred embodiment, slider 764 and pull wire 780 may be used to selectively collapse longitudinally collapsible portion 772 of elongate shaft 720.

Guidewire 704 extends distally away from hub 732 and wire lock 766. As shown in FIG. 13, a portion of guidewire 704 is disposed in a guidewire lumen 740 defined by a tubular member 734. A first end 736 of tubular member 734 is fixed to a wall 726 of proximal portion 770 of elongate shaft 720, and a second end 738 of tubular member 734 is disposed within shaft lumen 728 of elongate shaft 720. Guidewire lumen 740 is in fluid communication with a distal guidewire port 742 defined by second end 738 of tubular member 734. Catheter 702 also includes a proximal guidewire port 744 extending through wall 726 of proximal portion 770 of elongate shaft 720.

In FIG. 13, it may be appreciated that system 700 includes a filter 746 disposed within a distal portion 748 of shaft lumen 728. In the embodiment of FIG. 13, filter 746 is in a contracted configuration. System 700 may be utilized to deploy filter 746 into a blood vessel 730 as shown in FIG. 14.

Figure 14:
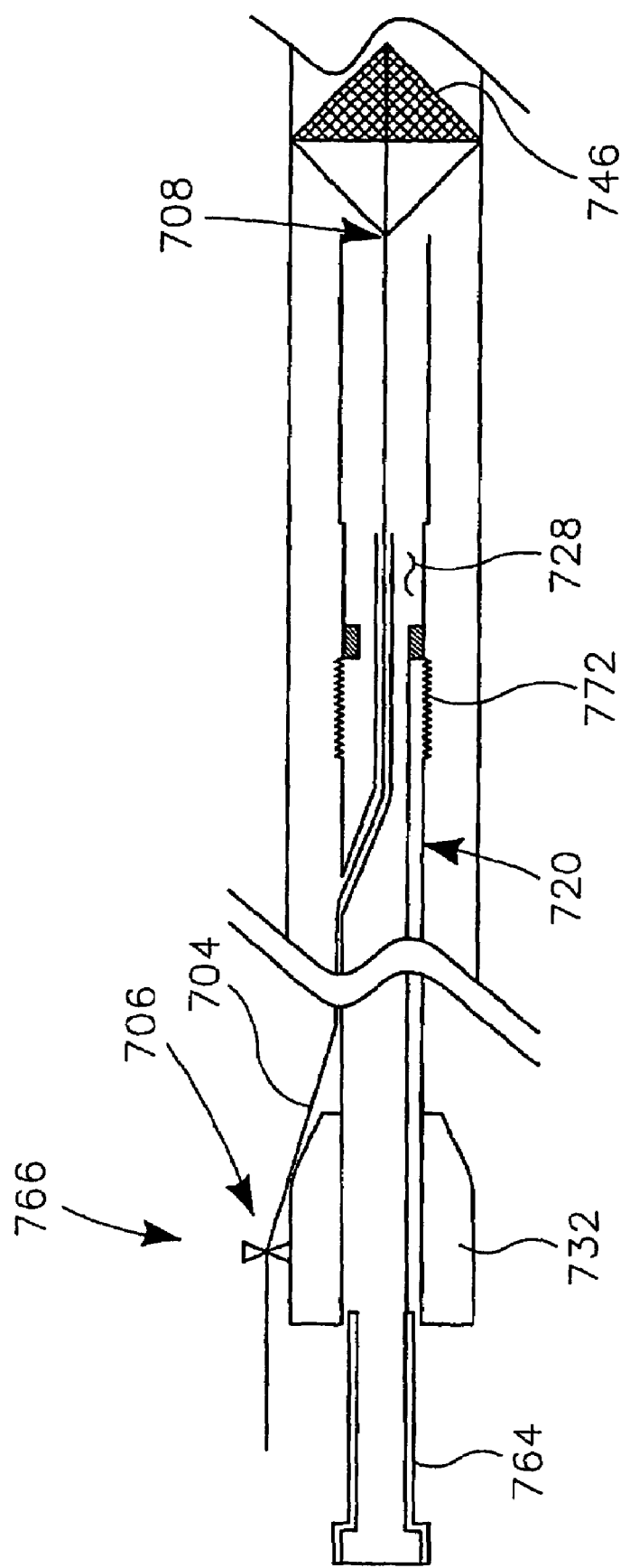
FIG. 14 is a partial cross-sectional view of the filter delivery system of FIG. 13.

FIG. 14 is a partial cross-sectional view of the filter delivery system 700 of FIG. 13. In the embodiment of FIG. 14, longitudinally collapsible portion 772 of elongate shaft 720 has been collapsed by urging slider 764 proximally relative to hub 732. In a preferred method in accordance with the present invention, guidewire 704 is held stationary while slider 764 is moved proximally.

As described previously, proximal portion 706 of guidewire 704 may be selectively fixed to hub 732 by wire lock 766, and filter 746 is fixed to a distal end 708 of guidewire 704. Thus, when collapsible portion 772 of elongate shaft 720 is collapsed, the longitudinal position of filter 746 is maintained by guidewire 704. In a preferred method, collapsible portion 772 is collapsed to the point that filter 746 is disposed outside of shaft lumen 728 as shown in FIG. 14.

Figure 15:
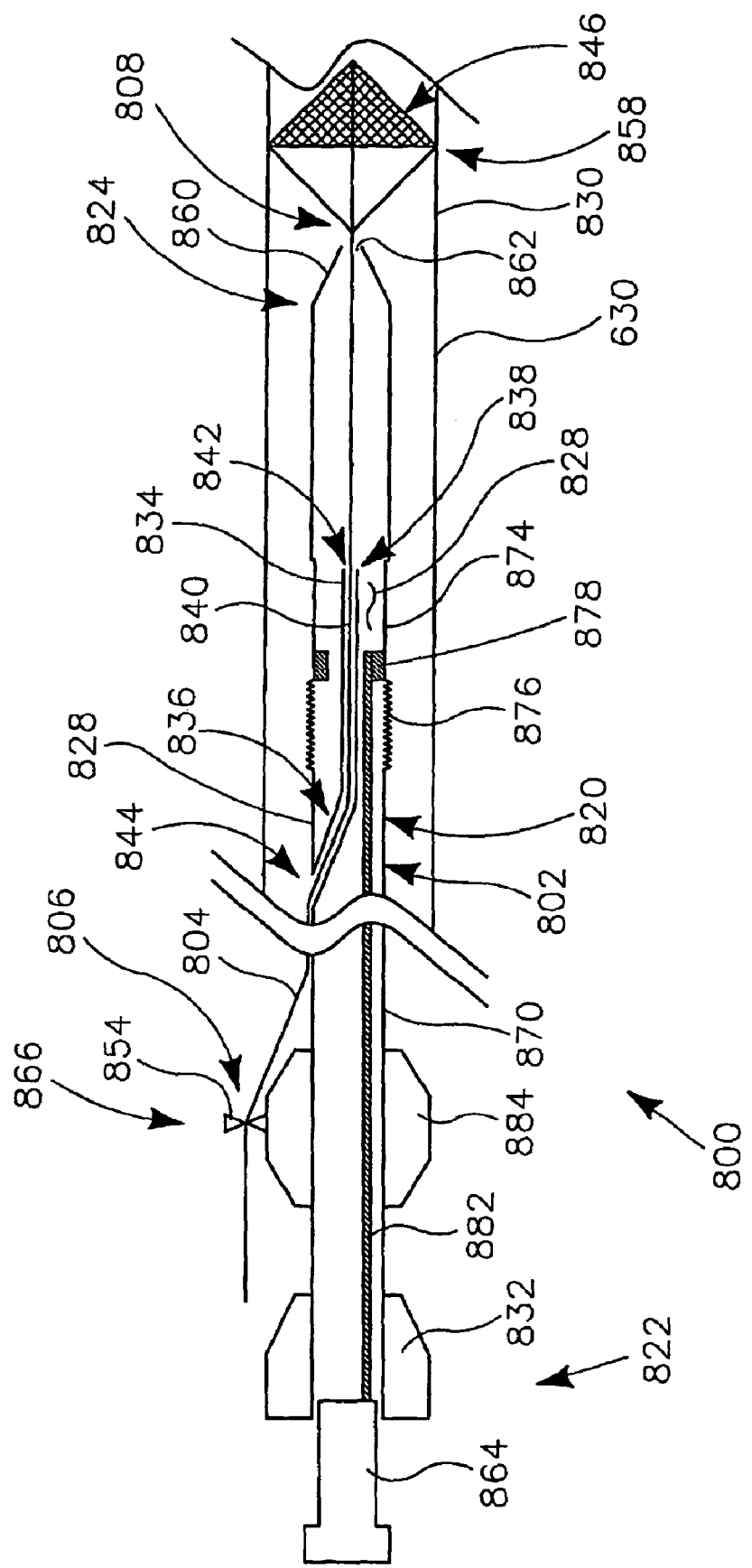
FIG. 15 is a partial cross-sectional view of a filter retrieval system in accordance with an additional exemplary embodiment of the present invention.

FIG. 15 is a partial cross-sectional view of a filter retrieval system 800 in accordance with an exemplary embodiment of the present invention. Filter retrieval system 800 includes a catheter 802 that may be utilized to retrieve a filter 846 that was previously delivered to a target location 858 in a blood vessel 830.

In the embodiment of FIG. 15, a distal end 808 of a guidewire 804 is fixed to filter 846. Guidewire 804 extends through a distal guidewire port 842, and a guidewire lumen 840 defined by a tubular member 834 of catheter 802. In the embodiment of FIG. 15, a first end 836 of tubular member 834 is fixed to a wall 826 of an elongate shaft 820 of catheter 802. A second end 838 of tubular member 834 is disposed within a shaft lumen 828 defined by wall 826 of elongate shaft 820.

Guidewire 804 also extends through a proximal guidewire port 844 extending through wall 826 of elongate shaft 820. Various embodiments of proximal guidewire port 844 are possible without deviating from the spirit and scope of the present invention. For example, proximal guidewire port 844 may be defined by wall 826 of elongate shaft 820. By way of a second example, proximal guidewire port 844 may be defined by first end 836 of tubular member 834.

Elongate shaft 820 of catheter 802 includes a proximal portion 870, a distal portion 874, and a longitudinally expandable portion 876 disposed between proximal portion 870 and distal portion 874. A ring 878 is fixed to distal portion 874 of elongate shaft 820 distally of expandable portion 876. A push rod 882 is disposed within shaft lumen 828 defined by elongate shaft 820. The distal end of push rod 882 is fixed to ring 878 and the proximal end of push rod 882 is fixed to a slider 864. Slider 864 is disposed in sliding engagement with a hub 832 which is disposed about a proximal end 822 of elongate shaft 820. In a preferred embodiment, slider 864 and push rod 882 may be used to selectively expand longitudinally expandable portion 876 of elongate shaft 820.

A grabber 884 is also disposed about elongate shaft 820. Grabber 884 may be used to assist a surgeon in grasping elongate shaft 820 of catheter 802. Grabber 884 includes a wire lock 866 having a plurality of jaws 854. Wire lock 866 may be used to selectively fix a proximal portion 806 of a guidewire 804 to grabber 884.

In the embodiment of FIG. 15, catheter 802 has been advanced along guidewire 804 until a distal end 824 of elongate shaft 820 is proximate filter 846. In FIG. 15, it may be appreciated that a cone 860 is disposed at distal end 824 of elongate shaft 820. The generally tapered shape of cone 860 may aid in advancing catheter 802 through a blood vessel 830. Cone 860 defines an aperture 862. Embodiments of cone 860 are possible in which cone 860 is adapted to fold proximally as filter 846 passes through aperture 862. Embodiments of cone 860 are also possible in which aperture 862 of cone 860 is adapted to expand radially as filter 846 passes therethrough.

Figure 16:
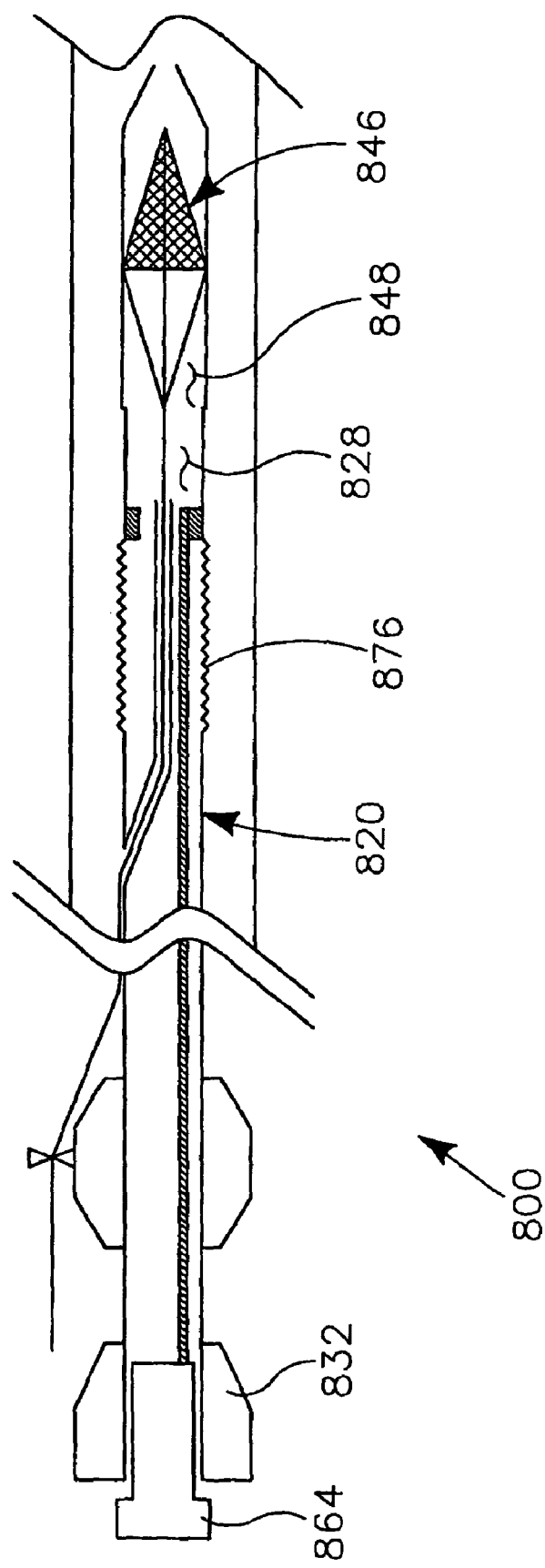
FIG. 16 is a partial cross-sectional view of the filter retrieval system of FIG. 15.

FIG. 16 is a partial cross-sectional view of the filter retrieval system 800 of FIG. 15. In the embodiment of FIG. 16, selectively expandable portion 876 of elongate shaft 820 has been expanded so that filter 846 is disposed within a distal portion 848 of shaft lumen 828. As shown in FIG. 16, filter 846 has been urged into a contracted configuration. In a preferred method in accordance with the present invention, a proximal portion 806 of guidewire 804 is fixed to grabber 884 using wire lock 866 prior to expanding longitudinally expandable portion 876. Expandable portion 876 may be expanded, for example, by urging slider 864 distally relative to hub 832.

Figure 17:
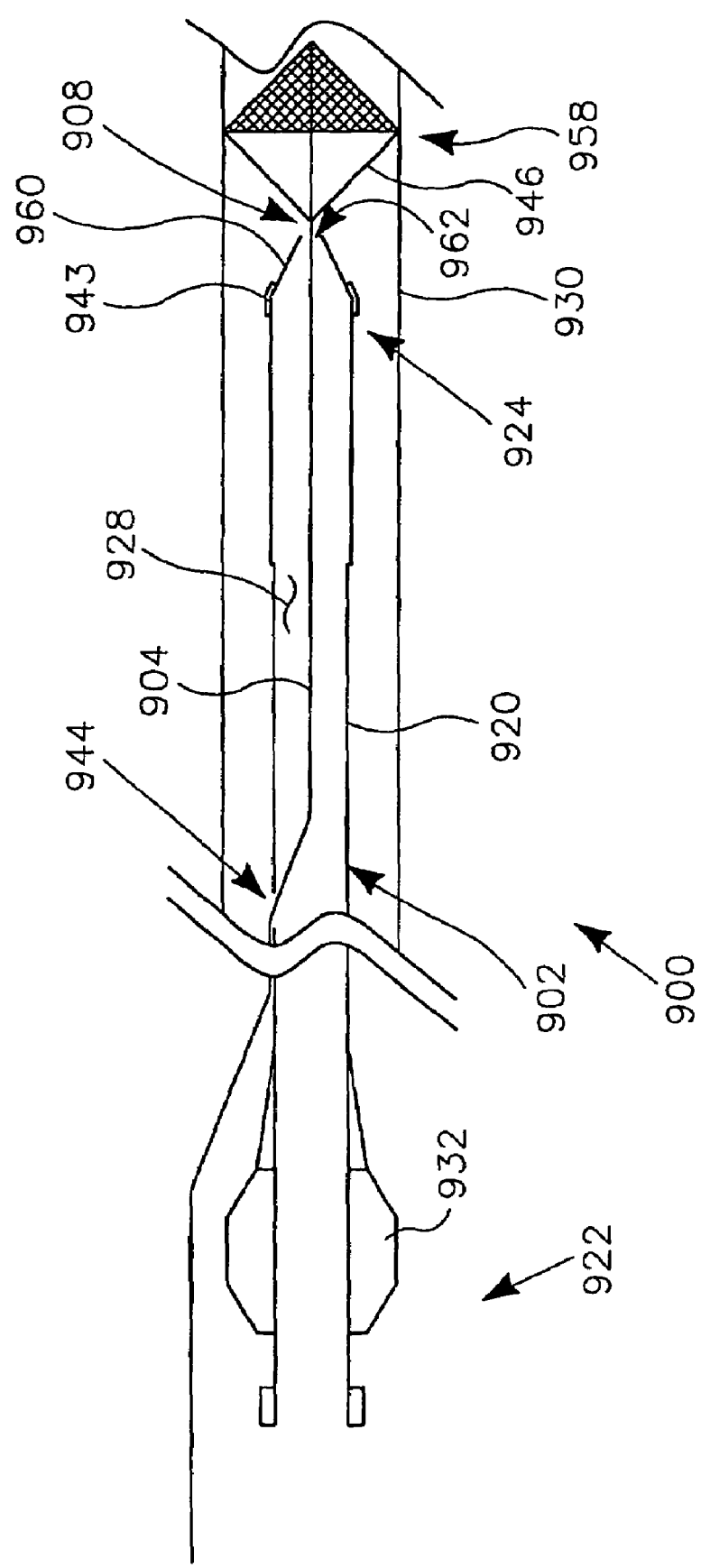
FIG. 17 is a partial cross-sectional view of a filter retrieval system in accordance with an exemplary embodiment of the present invention.

FIG. 17 is a partial cross-sectional view of a filter retrieval system 900 in accordance with an exemplary embodiment of the present invention. Filter retrieval system 900 includes a catheter 902 that may be utilized to retrieve a filter 946 that was previously delivered to a target location 958 in a blood vessel 930. Filter 946 may be delivered to target location, for example, using the filter delivery system of FIG. 1 and FIG. 2, and/or other filter delivery systems in accordance with the present invention. In FIG. 17 it may be appreciated that a distal end 908 of a guidewire 904 is fixed to filter 946.

In the embodiment of FIG. 17, guidewire 904 extends through a proximal guidewire port 944 and a shaft lumen 928 defined by an elongate shaft 920 of catheter 902. In the embodiment of FIG. 17, catheter 902 has been advanced along guidewire 904 until a distal end 924 of elongate shaft 920 is proximate filter 946. In FIG. 17, it may be appreciated that a cone 960 is disposed at distal end 924 of elongate shaft 920. In a preferred embodiment, cone 960 is fixed to elongate shaft 920 by a hinge 943. In a particularly preferred embodiment, hinge 943 comprises a flexible material, allowing hinge 943 to deflect as filter 946 is drawn through an aperture 962 defined by cone 960. Embodiments of cone 960 are possible in which hinge 943 and cone 960 are adapted to fold proximally as filter 946 passes through aperture 962.

In a preferred embodiment, catheter 902 extends out of blood vessel 930, so that a proximal end 922 of elongate shaft 920 is disposed outside the patient's body. As shown in FIG. 17, a hub 932 is disposed about elongate shaft 920 proximate proximal end 922. Hub 932 may aid a surgeon in grasping elongate shaft 920.

Figure 18:
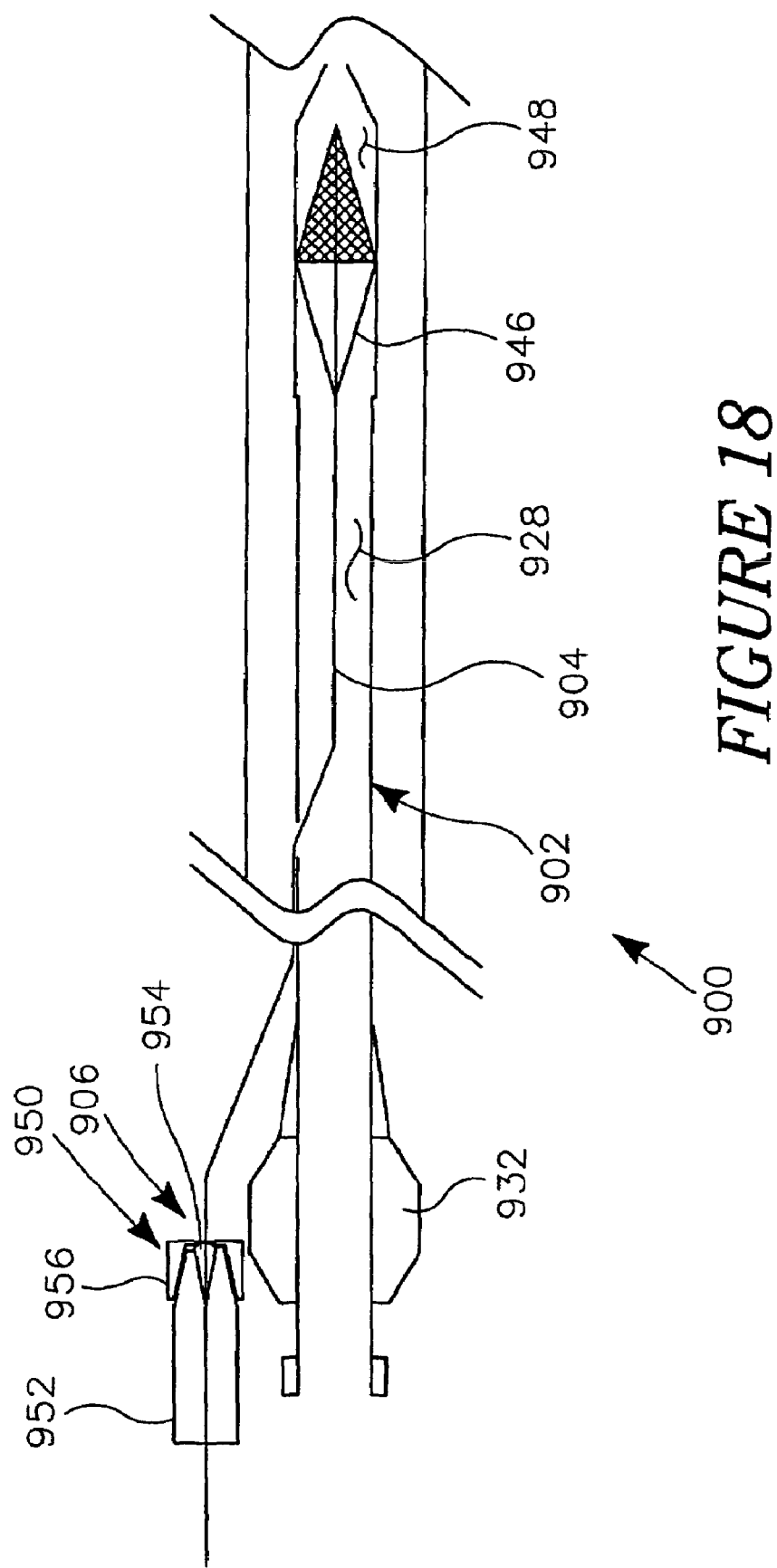
FIG. 18 is a partial cross-sectional view of the filter retrieval system illustrated in FIG. 17.

FIG. 18 is a partial cross-sectional view of the filter retrieval system 900 of FIG. 17. In the embodiment of FIG. 18, catheter 902 has been advanced distally relative to guidewire 904 so that filter 946 is disposed within a distal portion 948 of shaft lumen 928. As shown in FIG. 18, filter 946 has been urged into a contracted configuration. Catheter 902 may be moved relative to guidewire 904, for example, by grasping a proximal portion 906 of guidewire 904 and applying a pushing force to hub 932.

In the embodiment of FIG. 18, a wire gripper 950 is disposed about proximal portion 906 of guidewire 904. Wire gripper 950 includes a handle 952 and a plurality of jaws 954 for grasping guidewire 904. A knurl nut fitting 956 is used to selectively urge jaws 954 against guidewire 904. Wire gripper 950 may be used to assist a surgeon in grasping proximal portion 906 of guidewire 904.

Figure 19:
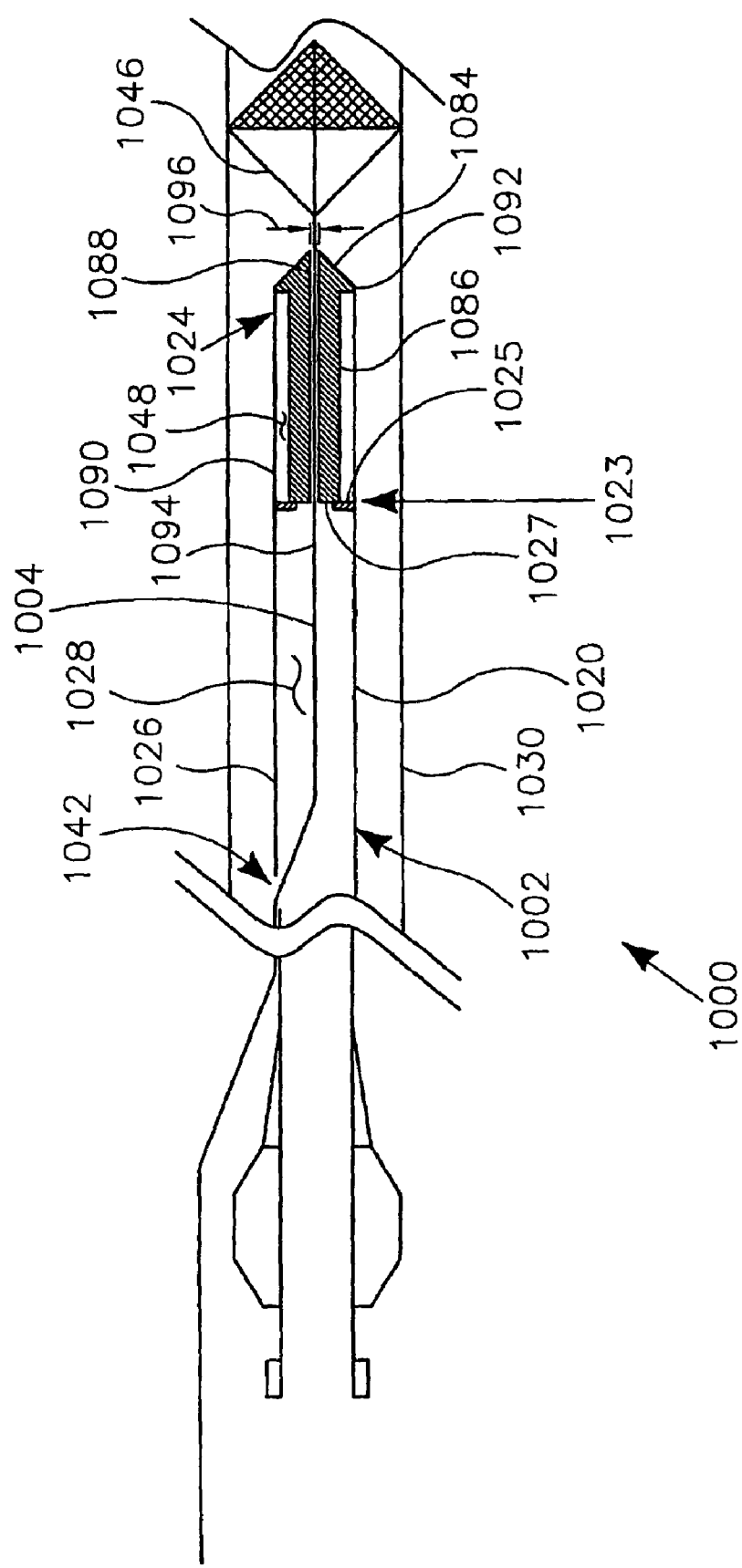
FIG. 19 is a partial cross-sectional view of a filter retrieval system in accordance with an exemplary embodiment of the present invention.

FIG. 19 is a partial cross-sectional view of a filter retrieval system 1000 in accordance with an exemplary embodiment of the present invention. Filter retrieval system 1000 includes a filter retrieval catheter 1002. In the embodiment of FIG. 19, a portion of filter retrieval catheter 1002 is disposed within a blood vessel 1030. Filter retrieval catheter 1002 includes an elongate shaft 1020 defining a shaft lumen 1028 having a distal portion 1048. A tip member 1086 is partially disposed within distal portion 1048 of shaft lumen 1028. A tapered distal portion 1084 of tip member 1086 extends distally beyond elongate shaft 1020. The generally conical shape of tapered distal portion 1084 may facilitate the tracking of filter retrieval catheter 1002 as it is advanced through blood vessel 1030.

Tip member 1086 defines a tip lumen 1088. In the embodiment of FIG. 19, a portion of a guidewire 1004 is disposed within tip lumen 1088. Guidewire 1004 extends through tip lumen 1088, a portion of shaft lumen 1028, and a proximal guidewire port 1042 defined by a wall 1026 of elongate shaft 1020. In the embodiment of FIG. 19, catheter 1002 has been advanced along guidewire 1004 until a distal end 1024 of elongate shaft 1020 is proximate a filter 1046 disposed within blood vessel 1030. Catheter 1002 may preferably be utilized to remove filter 1046 from blood vessel 1030 using methods in accordance with the present invention.

In a preferred embodiment, tip member 1086 is configured such that guidewire 1004 is substantially centered within elongate shaft 1020. Centering elongate shaft 1020 about guidewire 1004 may facilitate the tracking of filter retrieval catheter 1002 as it is advanced along a guidewire disposed within a blood vessel. Centering elongate shaft 1020 about guidewire 1004 may also reduced the magnitude of force which is required to urge elongate shaft 1020 over filter 1046 or other similar collapsible devices attached to guidewires.

Distal portion 1048 of shaft lumen 1028 has an inner diameter 1090. Tip member 1086 has an outer radial extent comprising an outer diameter 1092. In a preferred embodiment, outer diameter 1092 of tip member 1086 is similar to inner diameter 1090 of elongate shaft 1020. In a particularly preferred embodiment, outer diameter 1092 of tip member 1086 is slightly smaller than inner diameter 1090 of elongate shaft 1020.

In a preferred embodiment, tip lumen 1088 of tip member 1086 has a lumen diameter 1096 and guidewire 1004 has a guidewire diameter 1094. In a particularly preferred embodiment, lumen diameter 1096 is similar to guidewire diameter 1094. In a more particularly preferred embodiment, lumen diameter 1096 is slightly larger than guidewire diameter 1094.

The position of tip member 1086 shown in FIG. 19 may be referred to as an extended position. Tip member 1086 of filter retrieval catheter 1002 preferably also has a retracted position. Distal portion 1048 of shaft lumen 1028 and tip member 1086 are preferably configured such that a filter may be partially or completely disposed within distal portion 1048 of shaft lumen 1028 when tip member 1086 is in the retracted position.

When tip member 1086 is in the extended position, tapered distal portion 1084 of tip member 1086 preferably extends distally from distal portion 1048 of shaft lumen 1028. Filter retrieval catheter 1002 preferably includes a distal stop mechanism 1023 that is preferably biased to retain tip member 1086 in the extended position. In the embodiment of FIG. 19, distal stop mechanism 1023 includes a stop member 1025 that is preferably fixed to elongate shaft 1020 and a trailing surface 1027 of tip member 1086. As shown in FIG. 19, trailing surface 1027 preferably seats against stop member 1025 when tip member 1086 is in the extended position.

Figure 20:
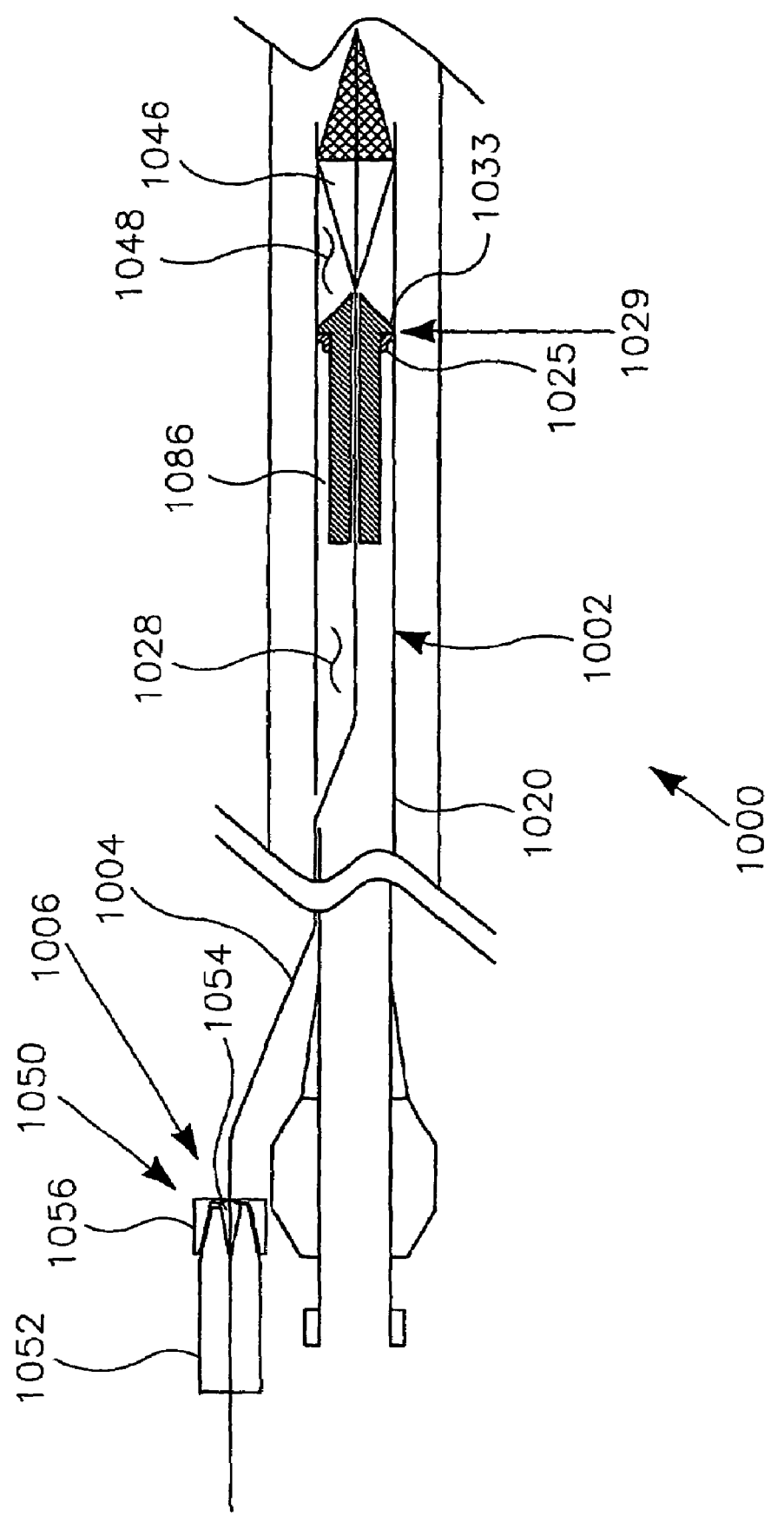
FIG. 20 is an additional partial cross-sectional view of filter retrieval system illustrated in FIG. 19.

FIG. 20 is an additional partial cross-sectional view of filter retrieval system 1000 of FIG. 19. In the embodiment of FIG. 20, tip member 1086 is disposed in the retracted position and filter 1046 is partially disposed within distal portion 1048 of shaft lumen 1028. Tip member 1086 and filter 1046 may be urged into distal portion 1048 of shaft lumen 1028, for example, by grasping guidewire 1004 and applying a distally directed pushing force to elongate shaft 1020. A wire gripper 1050 may assist a physician in grasping guidewire 1004. In the embodiment of FIG. 20, wire gripper 1050 is disposed about a proximal portion 1006 of guidewire 1004. Wire gripper 1050 includes a handle 1052 and a plurality of jaws 1054 for grasping guidewire 1004. A knurl nut fitting 1056 is used to selectively urge jaws 1054 against guidewire 1004. Wire gripper 1050 may be used to assist a surgeon in grasping proximal portion 1006 of guidewire 1004.

Filter retrieval catheter 1002 preferably includes a proximal stop mechanism 1029. In the embodiment of FIG. 20, proximal stop mechanism 1029 includes stop member 1025 that is preferably fixed to elongate shaft 1020 and a flange 1033 of tip member 1086. As shown in FIG. 20, flange 1033 preferably seats against stop member 1025 when tip member 1086 is in the retracted position. In FIG. 20, it may be appreciated that stop member 1025 may deflect when tip member 1086 is moved from the extended position to the retracted position. In a particularly preferred embodiment, proximal stop mechanism 1029 is adapted to provide a hard stop that may be sensed by a physician using filter retrieval catheter 1002 in a surgical procedure. This hard stop provides tactile feedback indicating that tip member 1086 has been successfully placed in the retracted position.

In FIG. 20, it may be appreciated that filter 1046 has been urged into a contracted configuration. As described above, filter retrieval catheter 1002 preferably includes a proximal stop mechanism 1029 that is adapted to stop relative movement between tip member 1086 and elongate shaft 1020 when tip member 1086 is in the retracted position. In a particularly preferred embodiment, the relative movement required to move tip member 1086 from the extended position to the retracted position is similar to the relative movement required to urge filter 1046 into distal portion 1048 of shaft lumen 1028 and into a contracted configuration. Also in a particularly preferred embodiment, proximal stop mechanism 1029 is adapted to provide a hard stop that provides tactile feedback indicating that tip member 1086 has been successfully placed in the retracted position and filter 1046 has been successfully urged into a contracted configuration. When a physician feels this hard stop, he or she will know that filter 1046 has been urged into a retracted position, and the likelihood that a physician will attempt to withdraw filter 1046 from blood vessel 1030 while it is in an expanded condition is reduced.

Figure 21:
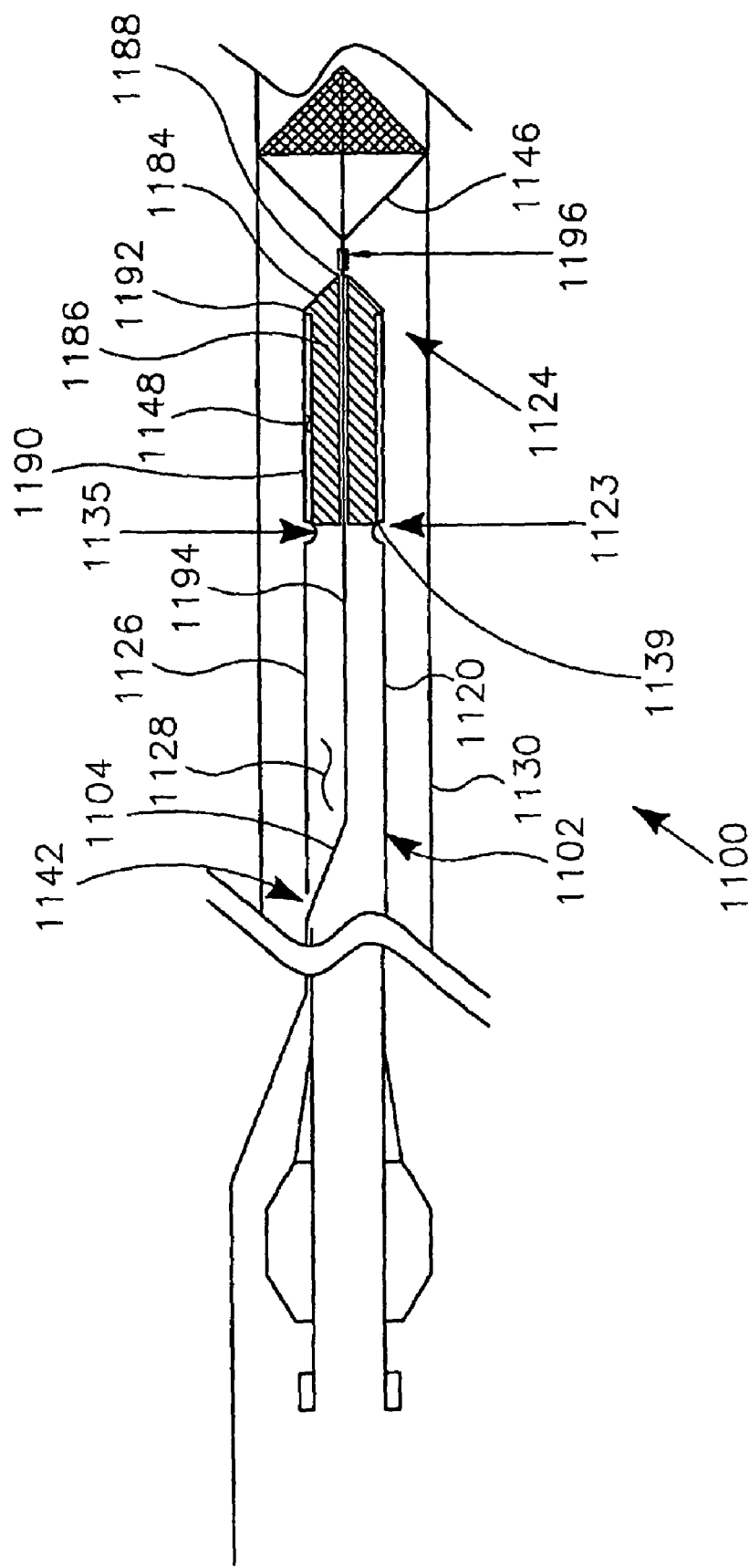
FIG. 21 is a partial cross-sectional view of a filter retrieval system in accordance with an exemplary embodiment of the present invention.

FIG. 21 is a partial cross-sectional view of a filter retrieval system 1100 in accordance with an exemplary embodiment of the present invention. Filter retrieval system 1100 includes a filter retrieval catheter 1102. In the embodiment of FIG. 21, a portion of filter retrieval catheter 1102 is disposed within a blood vessel 1130. Filter retrieval catheter 1102 includes an elongate shaft 1120 defining a shaft lumen 1128 having a distal portion 1148. A tip member 1186 is partially disposed within distal portion 1148 of shaft lumen 1128. A tapered distal portion 1184 of tip member 1186 extends distally beyond elongate shaft 1120. The generally conical shape of tapered distal portion 1184 may facilitate the tracking of filter retrieval catheter 1102 as it is advanced through blood vessel 1130.

Tip member 1186 defines a tip lumen 1188. In the embodiment of FIG. 21, a portion of a guidewire 1104 is disposed within tip lumen 1188. Guidewire 1104 extends through tip lumen 1188, a portion of shaft lumen 1128, and a proximal guidewire port 1142 defined by a wall 1126 of elongate shaft 1120. In the embodiment of FIG. 21, catheter 1102 has been advanced along guidewire 1104 until a distal end 1124 of elongate shaft 1120 is proximate a filter 1146 disposed within blood vessel 1130. Catheter 1102 may preferably be utilized to remove filter 1146 from blood vessel 1130 using methods in accordance with the present invention.

In a preferred embodiment, tip member 1186 is configured such that guidewire 1104 is substantially centered within elongate shaft 1120. Centering elongate shaft 1120 about guidewire 1104 may facilitate the tracking of filter retrieval catheter 1102 as it is advanced along a guidewire disposed within a blood vessel. Centering elongate shaft 1120 about guidewire 1104 may also reduced the magnitude of force which is required to urge elongate shaft 1120 over filter 1146 or other similar collapsible devices attached to guidewires.

Distal portion 1148 of shaft lumen 1128 has an inner diameter 1190. Tip member 1186 has an outer radial extent comprising an outer diameter 1192. In a preferred embodiment, outer diameter 1192 of tip member 1186 is similar to inner diameter 1190 of elongate shaft 1120. In a particularly preferred embodiment, outer diameter 1192 of tip member 1186 is slightly smaller than inner diameter 1190 of elongate shaft 1120.

In a preferred embodiment, tip lumen 1188 of tip member 1186 has a lumen diameter 1196 and guidewire 1104 has a guidewire diameter 1194. In a particularly preferred embodiment, lumen diameter 1196 is similar to guidewire diameter 1194. In a more particularly preferred embodiment, lumen diameter 1196 is slightly larger than guidewire diameter 1194.

The position of tip member 1186 shown in FIG. 21 may be referred to as an extended position. Tip member 1186 of filter retrieval catheter 1102 preferably also has a retracted position. Distal portion 1148 of shaft lumen 1128 and tip member 1186 are preferably configured such that a filter may be partially or completely disposed within distal portion 1148 of shaft lumen 1128 when tip member 1186 is in the retracted position.

When tip member 1186 is in the extended position, tapered distal portion 1184 of tip member 1186 preferably extends distally from distal portion 1148 of shaft lumen 1128. Filter retrieval catheter 1102 preferably includes a distal stop mechanism 1123 that is preferably biased to retain tip member 1186 in the extended position. In the embodiment of FIG. 21, distal stop mechanism 1123 includes an annular bead 1135 formed by wall 1126 of elongate shaft 1120 and a trailing edge 1139 of tip member 1186. As shown in FIG. 21, trailing edge 1139 preferably seats against annular bead 1135 when tip member 1186 is in the extended position.

Figure 22:
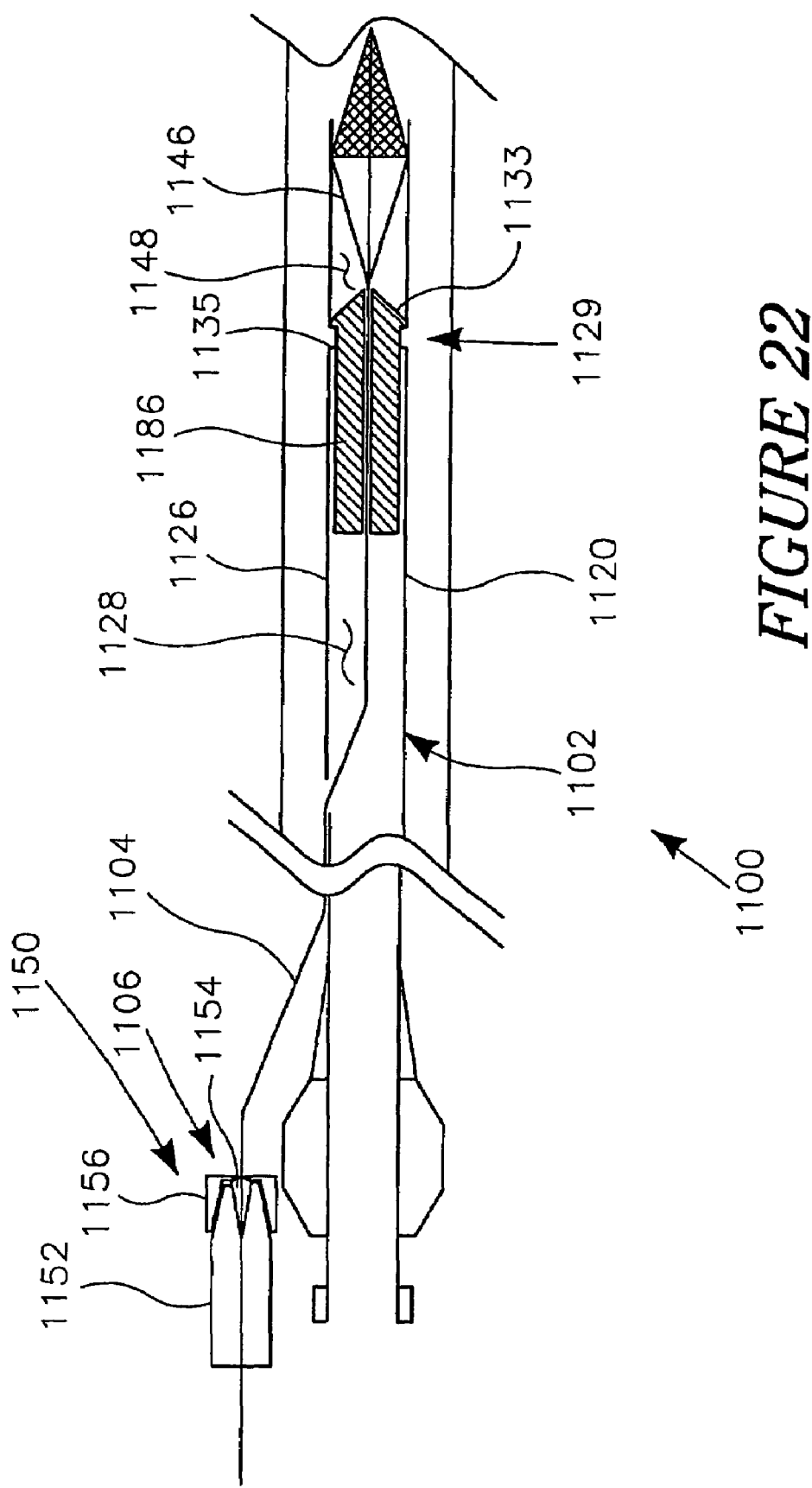
FIG. 22 is an additional partial cross-sectional view of filter retrieval system illustrated in FIG. 21.

FIG. 22 is an additional partial cross-sectional view of filter retrieval system 1100 of FIG. 21. In the embodiment of FIG. 22, tip member 1186 is disposed in the retracted position and filter 1146 is partially disposed within distal portion 1148 of shaft lumen 1128. Tip member 1186 and filter 1146 may be urged into distal portion 1148 of shaft lumen 1128, for example, by grasping guidewire 1104 and applying a distally directed pushing force to elongate shaft 1120. A wire gripper 1150 may assist a physician in grasping guidewire 1104. In the embodiment of FIG. 22, wire gripper 1150 is disposed about a proximal portion 1106 of guidewire 1104. Wire gripper 1150 includes a handle 1152 and a plurality of jaws 1154 for grasping guidewire 1104. A knurl nut fitting 1156 is used to selectively urge jaws 1154 against guidewire 1104. Wire gripper 1150 may be used to assist a surgeon in grasping proximal portion 1106 of guidewire 1104.

Filter retrieval catheter 1102 preferably includes a proximal stop mechanism 1129. In the embodiment of FIG. 22, proximal stop mechanism 1129 includes annular bead 1135 formed by wall 1126 of elongate shaft 1120 and a flange 1133 of tip member 1186. As shown in FIG. 22, flange 1133 preferably seats against annular bead 1135 when tip member 1186 is in the retracted position. In FIG. 22, it may be appreciated that annular bead 1135 may deflect when tip member 1186 is moved from the extended position to the retracted position. In a particularly preferred embodiment, proximal stop mechanism 1129 is adapted to provide a hard stop that may be sensed by a physician using filter retrieval catheter 1102 in a surgical procedure. This hard stop provides tactile feedback indicating that tip member 1186 has been successfully placed in the retracted position.

In FIG. 22, it may be appreciated that filter 1146 has been urged into a contracted configuration. As described above, filter retrieval catheter 1102 preferably includes a proximal stop mechanism 1129 that is adapted to stop relative movement between tip member 1186 and elongate shaft 1120 when tip member 1186 is in the retracted position. In a particularly preferred embodiment, the relative movement required to move tip member 1186 from the extended position to the retracted position is similar to the relative movement required to urge filter 1146 into distal portion 1148 of shaft lumen 1128 and into a contracted configuration. Also in a particularly preferred embodiment, proximal stop mechanism 1129 is adapted to provide a hard stop that provides tactile feedback indicating that tip member 1186 has been successfully placed in the retracted position and filter 1146 has been successfully urged into a contracted configuration. When a physician feels this hard stop, he or she will know that filter 1146 has been urged into a retracted position, and the likelihood that a physician will attempt to withdraw filter 1146 from blood vessel 1130 while it is in an expanded condition is reduced.

Figure 23:
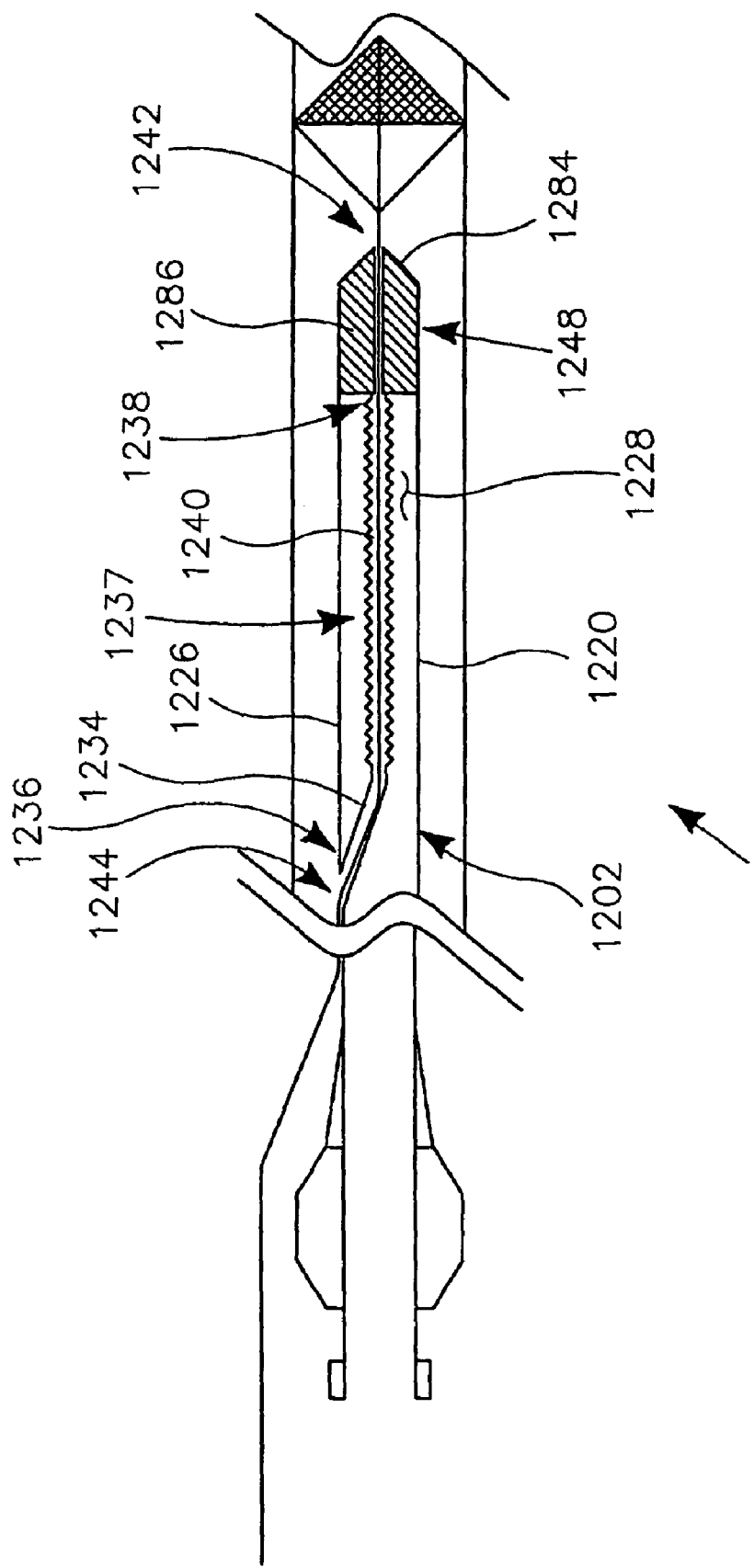
FIG. 23 is a partial cross-sectional view of a filter retrieval system in accordance with an exemplary embodiment of the present invention.

FIG. 23 is a partial cross-sectional view of a filter retrieval system 1200 in accordance with an exemplary embodiment of the present invention. Filter retrieval system 1200 includes a filter retrieval catheter 1202. Filter retrieval catheter 1202 includes an elongate shaft 1220 and a tubular member 1234. A first end 1236 of tubular member 1234 is fixed to a wall 1226, and a second end 1238 of tubular member 1234 is preferably fixed to a tip member 1286 of filter retrieval catheter 1202. Tip member 1286 is slidingly disposed within a distal portion 1248 of a shaft lumen 1228 defined by elongate shaft 1220.

Filter retrieval catheter 1202 includes a distal guidewire port 1242 defined by tip member 1286 and a proximal guidewire port 1244 extending through wall 1226 of elongate shaft 1220. Various embodiments of proximal guidewire port 1244 are possible without deviating from the spirit and scope of the present invention. For example, proximal guidewire port 1244 may be defined by wall 1226 of proximal portion 1270 of elongate shaft 1220. By way of a second example, proximal guidewire port 1244 may be defined by first end 1236 of tubular member 1234. Tubular member 1234 defines a guidewire lumen 1240 which is in fluid communication with proximal guidewire port 1244 and distal guidewire port 1242.

Tubular member 1234 preferably includes a longitudinally collapsible portion 1237 disposed between first end 1236 and second end 1238. In the embodiment of FIG. 23, collapsible portion 1237 is in an extended state and tip member 1286 disposed in an extended position. Collapsible portion 1237 preferably also has a contracted state. In a preferred embodiment, tip member 1286 is disposed in a retracted position when collapsible portion 1237 is in a contracted state. Distal portion 1248 of shaft lumen 1228 and tip member 1286 are preferably configured such that a filter may be partially or completely disposed within distal portion 1248 of shaft lumen 1228 when tip member 1286 is in the retracted position. When tip member 1286 is in the extended position, tapered distal portion 1284 of tip member 1286 preferably extends distally from distal portion 1248 of shaft lumen 1228.

Figure 24:
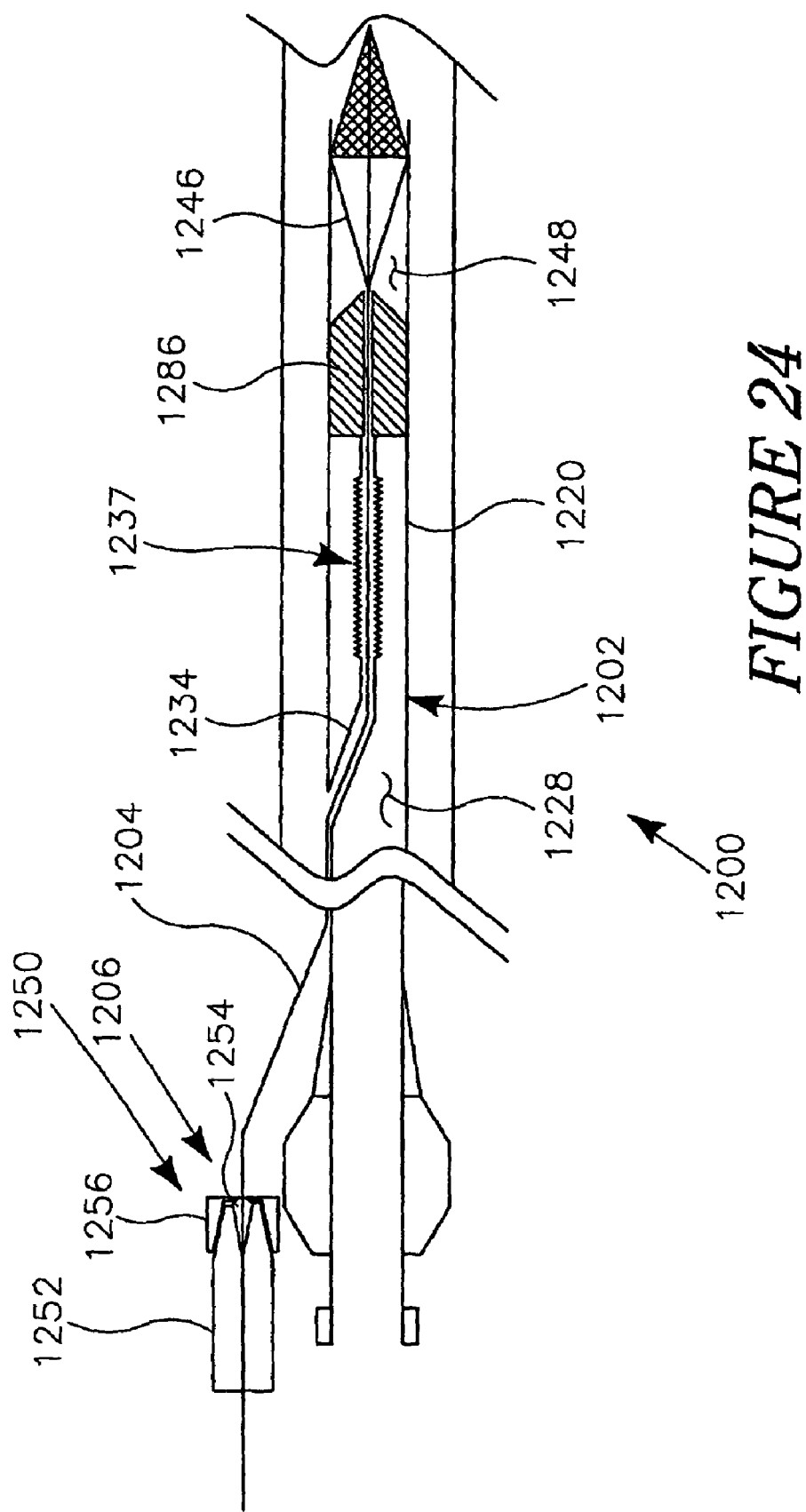
FIG. 24 is an additional partial cross-sectional view of filter retrieval system illustrated in FIG. 23.

FIG. 24 is an additional partial cross-sectional view of filter retrieval system 1200 of FIG. 23. In the embodiment of FIG. 24, tip member 1286 is disposed in the retracted position and collapsible portion 1237 of tubular member 1234 is in a contracted state. Also in the embodiment of FIG. 24, filter 1246 is partially disposed within distal portion 1248 of shaft lumen 1228.

One method in accordance with the present invention may include the steps of grasping guidewire 1204 near the proximal end thereof and applying a distally directed pushing force to elongate shaft 1220 near the proximal end thereof. This application of force to proximal portions of filter retrieval catheter 1202 may be used to urge collapsible portion 1237 of tubular member 1234 into a contracted state, to urge tip member 1286 and filter 1246 into distal portion 1248 of shaft lumen 1228, and to urge filter 1246 into a contracted configuration. A wire gripper 1250 may assist a physician in grasping guidewire 1204. In the embodiment of FIG. 24, wire gripper 1250 is disposed about a proximal portion 1206 of guidewire 1204. Wire gripper 1250 includes a handle 1252 and a plurality of jaws 1254 for grasping guidewire 1204. A knurl nut fitting 1256 is used to selectively urge jaws 1254 against guidewire 1204.

Having thus described the preferred embodiments of the present invention, those of skill in the art will readily appreciate that yet other embodiments may be made and used within the scope of the claims hereto attached. Numerous advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The invention's scope is, of course, defined in the language in which the appended claims are expressed.

What is claimed is:

1. A filter retrieval system comprising:
    a catheter including an elongate shaft having a proximal end, a distal end, and a wall defining a shaft lumen;
    a proximal guidewire port disposed distal of the proximal end of the elongate shaft;
    a generally conical tip disposed near the distal end of the elongate shaft, the conical tip having an aperture defining a distal guidewire port, the generally conical tip comprising a flexible tip member, at least a portion of the flexible tip member disposed within the shaft lumen;

a guidewire extending through the distal guidewire port and the proximal guidewire port;

a filter coupled to the guidewire; a wire gripper, wherein the wire gripper comprises a plurality of jaws for grasping the guidewire.

2. The system of claim 1, wherein the flexible tip member is moveable relative to the elongate shaft.

3. The system of claim 2, wherein the flexible tip member moves between an extended position and a retracted position.

4. The system of claim 1, wherein the generally conical tip has a generally tapered shape.

5. The system of claim 1, wherein the elongate shaft further comprises a proximal stop mechanism disposed in a distal portion of the shaft lumen.

6. The system of claim 5, wherein the proximal stop mechanism limits retraction of the flexible tip member within the shaft lumen.

7. The system of claim 5, wherein the flexible tip member seats against the stop mechanism when the tip member is in a retracted position.

8. The system of claim 5, wherein the proximal stop mechanism comprises a stop member.

9. A catheter system for retrieving a filter, comprising:

an elongate shaft having a proximal end, a distal end, and a wall defining a shaft lumen, the shaft lumen having a diameter sized to accommodate a filter;

a proximal guidewire port disposed distal of the proximal end of the elongate shaft; and a generally conical tip having an outer diameter and an aperture defining a distal guidewire port connected to a portion of the elongate shad proximate the distal end of the elongate shaft;

wherein the outer diameter of the generally conical tip is slightly smaller than the diameter of the shaft lumen such that the generally conical tip is retractable into the shaft lumen a guidewire extending through the distal guidewire port and the proximal guidewire port; the filter coupled to the guidewire; a wire gripper, wherein the wire gripper comprises a plurality of jaws for grasping the guidewire.

10. The system of claim 9, wherein the generally conical tip comprises a flexible tip member.

11. The system of claim 10, wherein at least a portion of the flexible tip member is disposed within the shaft lumen.

12. The system of claim 10, wherein the flexible tip member is moveable relative to the elongate shaft.

13. The system of claim 12, wherein the flexible tip member moves between an extended position and a retracted position.

14. The system of claim 10, wherein the elongate shaft further comprises a proximal stop mechanism disposed in a portion of the shaft lumen.

15. The system of claim 14, wherein the proximal stop mechanism limits retraction of the flexible tip member within the shaft lumen.

16. The system of claim 14, wherein the flexible tip member seats against the stop mechanism when the tip member is in a retracted position.

17. The system of claim 14, wherein the proximal stop mechanism comprises a stop member.

18. The system of claim 9, wherein the generally conical tip has a generally tapered shape.

* * * * *